(12) United States Patent
Cheng et al.

(10) Patent No.: US 10,287,620 B2
(45) Date of Patent: May 14, 2019

(54) DIGITAL POLYMERASE FIDELITY ASSAY

(71) Applicant: Bio-Rad Laboratories, Inc., Hercules, CA (US)

(72) Inventors: Man Cheng, Hercules, CA (US); Xiangdong Meng, Hercules, CA (US); Jan Zur Megede, Hercules, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 32 days.

(21) Appl. No.: 15/581,401

(22) Filed: Apr. 28, 2017

(65) Prior Publication Data

US 2017/0314060 A1    Nov. 2, 2017

Related U.S. Application Data

(60) Provisional application No. 62/329,733, filed on Apr. 29, 2016.

(51) Int. Cl.
*C12N 15/62* (2006.01)
*C12Q 1/48* (2006.01)

(52) U.S. Cl.
CPC .............. *C12Q 1/485* (2013.01); *C12Q 1/48* (2013.01); *G01N 2333/9126* (2013.01); *G01N 2333/9128* (2013.01); *G01N 2333/91245* (2013.01)

(58) Field of Classification Search
CPC ............ C12Q 1/6874; C12Q 2521/101; C12N 9/1252; C12N 15/62; C12N 15/64
See application file for complete search history.

(56) References Cited

U.S. PATENT DOCUMENTS

| 6,383,755 B1 | 5/2002 | Davis et al. |
| 2004/0137480 A1* | 7/2004 | Eglen .................... C12N 15/62 435/6.11 |
| 2013/0059754 A1 | 3/2013 | Tzonev et al. |
| 2014/0227705 A1 | 8/2014 | Vogelstein et al. |
| 2014/0309128 A1 | 10/2014 | Regan et al. |

FOREIGN PATENT DOCUMENTS

WO    2016/060714 A1    4/2016

OTHER PUBLICATIONS

Yang et al. 2003; A fluorimetric method using fluorescein di-b-D-galactopyranoside for quantifying the senescence-associated b-galactosidase activity in human foreskin fibroblast Hs68 cells. Analytical Chemistry. 325: 337-343.*
Keith et al. "A plasmid-based lacZa gene assay for DNA polymerase fidelity measurement," Anal Biochem, Feb. 15, 2013: 433(2): 153-161.
Kunkel et al. "The Mutational Specificity of DNA Polymerase-β during in Vitro DNA Synthesis," *The Journal of Biological Chemistry*, 1985, vol. 260, No. 9, Issue May 10, pp. 5787-5796.
Kunkel et al. "The Mutational Specificity of DNA Polymerases-α and -γ during in Vitro DNA Synthesis," *The Journal of Biological Chemistry*, 1985, vol. 260, No. 23, pp. 12866-12874.
Fortune et al. "*Saccharomyces cerevisiae* DNA Polymerase δ; High Fidelity for Base Substitutes But Lower Fidelity for Single and Multi-Base Deletions," The Journal of Biological Chemistry, Aug. 19, 2005, vol. 280, No. 33, pp. 29980-29987.
Jozwiakowski et al. "Plasmid-based lacZα assay for DNA polymerase fidelity: application to archaeal family-B DNA polymerase," Nucleic Acids Research, Jun. 10, 2009, vol. 37, No. 15, 7 pp.
International Search Report and Written Opinion in PCT/US2017/030073; 17 pages; dated Aug. 3, 2017.
Lee, et al.; "Recovery of Plasmid pEMB1, Whose Toxin-Antitoxin System Stabilizes an Ampicillin Resistance-Conferring Beta-Lactamase Gene in *Escherichia coli*, From Natural Environmenta"; *Appl. Environ. Microbiol.*; vol. 81, No. 1; Jan. 2015; pp. 40-47.

* cited by examiner

*Primary Examiner* — Karen Cochrane Carlson
(74) *Attorney, Agent, or Firm* — Kilpatrick Townsend and Stockton LLP

(57) ABSTRACT

Methods of determining polymerase fidelity are provided. In one embodiment, the method comprises filling a gapped plasmid with a polymerase to form a gap-filled plasmid, wherein the gap-filled plasmid comprises a gene encoding an protein that is functional or non-functional depending on the polymerase fidelity; forming a plurality of partitions from a solution comprising the gap-filled plasmid and a label for detecting the presence of the plasmid; detecting the presence of the gap-filled plasmid in one or more of the partitions; and determining the fidelity of the polymerase by determining a ratio of partitions containing the gene encoding a functional protein to partitions containing a gene encoding a non-functional protein.

50 Claims, 9 Drawing Sheets

Specification includes a Sequence Listing.

| FDG/IPTG: | + | + | + |
| JM109 cell: | + | + | − |
| pUC19: | − | − | − |
| pET11: | − | + | − |

SEQUENCE LISTING

<160> NUMBER OF SEQ ID NOS: 1

<210> SEQ ID NO 1
<211> LENGTH: 594
<212> TYPE: DNA
<213> ORGANISM: Artificial Sequence
<220> FEATURE:
<223> OTHER INFORMATION: Synthetic construct

<400> SEQUENCE: 1

```
atcgatcctc agcgcaacgc aattaatgtg agttagctca ctcattaggc acccaggct      60 ttacacttta tgcttccggc tcgtatgttg tgtggaattg tgagcggata acaatttcac    120
acaggaaaca gctatgacca tgattacgaa ttcactggcc gtcgttttac aacgtcgtga    180
ctgggaaaac cctggcgtta cccaacttaa tcgccttgca gcacatcccc ctttcgccag    240
ctggcgtaat agcgaagagg cccgcaccga ccgcccttcc caacagttgc gcagcctcag    300
cggcgaatgg cgctttgcct ggtttccggc accagaagcg gtgccggaaa gctggctgga    360
gtgcgatctt cctgaggccg atacggtcgt cgtccctca aactggcaga tgcacggtta     420
cgatgcgccc atctacacca acgtaaccta tcccattacg gtcaatccgc cgtttgttcc    480
cacggagaat ccgacgggtt gttactcgct cacatttaat gttgatgaaa gctggctaca    540
ggaaggccag acgcgaatta tttttgatgg cgttcctatt ggttaatgct taag          594
```

DIGITAL POLYMERASE FIDELITY ASSAY

This application claims the benefit of U.S. Provisional Application 62/329,733 filed on Apr. 29, 2016 which is hereby incorporated by reference in its entirety.

BACKGROUND

DNA polymerases are used in many biotechnological applications such as DNA sequencing and the polymerase chain reaction. DNA polymerases that have high accuracy or fidelity are desired for these applications. A simple method for measuring the fidelity of the DNA polymerases is therefore also desired.

One common approach to measure fidelity uses a polymerase to fill a gap in the bacteriophage M13mp2 lacZα gene fragment, which encodes the α-peptide, an inactive segment of β-galactosidase. When accurately copied, and subsequently introduced into *E. coli* that bears a complementing copy of the remaining β-galactosidase gene, functional β-galactosidase is reconstituted, resulting in the hydrolysis of X-gal and blue bacterial plaques (see Bebenek K., Kunkel T. A. *Methods Enzymol.* 1995; 262:217-232). Inaccurate polymerase activity may result in a defective α-peptide, eventually resulting in reduced or abolished β-galactosidase activity, indicated by light blue or colorless β-galactosidase activity, indicated by light blue or colorless plaques. The error rate is calculated from the blue/colorless plaque ratio, and mutations can be determined by DNA sequencing. Although this method is widely used to assess DNA polymerase fidelity, the method is labor and time intensive.

A plasmid-based DNA polymerase assay has also been developed (see Keith B. J., Jozwiakowski S. K., and Connolly B. A. *Anal. Biochem.* 2013 Feb. 15; 433(2): 153-161). The assay is based on gapped plasmid containing the lacZα reporter gene in a single-stranded region. Nicking at two sites flanking lacZa, and removing the excised strand by thermocycling in the presence of complementary competitor DNA, is used to generate the gap. The accuracy of a polymerase can be determined by copying the gene in vitro and then introducing the plasmid into *E. coli*, an approach similar in concept to that described above for the bacteriophage system. The error rate is again calculated from the blue/colorlessplaque ratio. The plasmid system is an improvement over the bacteriophage system with respect to the gapped DNA template preparation step but the blue/ colorless colony scoring step remains time-consuming and tedious.

SUMMARY

Disclosed herein are methods of determining polymerase fidelity. In some embodiments, the method comprises filling a gapped plasmid with a polymerase to form a gap-filled plasmid, wherein the gap-filled plasmid comprises a gene encoding a protein that is functional or non-functional depending on the polymerase fidelity; forming a plurality of partitions from a solution comprising a polymerase gap-filled plasmid and a label for detecting the presence of the gap-filled plasmid; detecting the presence of the gap-filled plasmid in one or more of the partitions; and determining the polymerase fidelity by determining a ratio of partitions containing the gene encoding the functional protein to partitions containing a gene encoding a non-functional protein. In some embodiments, a toxin and an antitoxin are the proteins encoded by the genes in the gap-filled plasmid. In some embodiments, the protein is an enzyme selected from the group consisting of beta-galactosidase, luciferase, and a target specific protease. In some embodiments in which the enzyme is beta-galactosidase, the partition includes an inducer selected from the group consisting of isopropyl beta-D-1-thiogalactopyranoside (IPTG), methyl-beta-D-1-thiogalactopyranoside, lactose and lactose derivatives. In embodiments in which the enzyme is beta-galactosidase, the substrate is selected from the group consisting of fluorescein di-(beta-D-galactopyranoside), naphthofluorescein di-(beta-D-galactopyranoside), (9H-(1,3-dichloro-9,9-dimethylacridin-2-one-7-yl) beta-D-galactopyranoside), 4-methylumbelliferyl beta-D-galactopyranoside, and resorufin beta-D-galactopyranoside. In some embodiments, the label for detecting the presence of the plasmid is selected from the group consisting of a fluorophore, biotin, a fluorescent protein encoded by the plasmid, and a protein encoded by the plasmid. In some embodiments, the gap-filled plasmid is transformed into a cell prior to forming the plurality of partitions and each of the partitions comprises an indicator for detecting the presence of the cell. In certain embodiments, the indicator is selected from the group consisting of a fluorescent protein, an enzyme, an auto-fluorescent protein, a live cell-staining dye, or a nuclease alert reagent, and antibiotic-resistance. In some embodiments, the fluorescent protein is selected from the group consisting of an mKO fluorescent protein, a green fluorescent protein, a cyan fluorescent protein, a red fluorescent protein, red fluorescent protein variants, and a yellow fluorescent protein. In certain embodiments, the gap-filled plasmid comprises a gene segment encoding for the fluorescent protein.

In some embodiments in which the gap-filled plasmid is in a cell, the method further comprises incubating the solution or the partitions at a temperature to grow the cells and to express the enzyme before or after forming the partitions. In some embodiments, the cell is selected from the group consisting of a bacterial cell, a mammalian cell, a yeast cell, and an insect cell. In certain embodiments, the gap-filled plasmid is in a cell-free expression system. In some embodiments, the polymerase is a DNA polymerase. In some embodiments, the polymerase is a reverse transcriptase. In certain embodiments, the plasmid is selected from the group consisting of double-stranded DNA plasmid, double-stranded RNA plasmid, a DNA/RNA hybrid plasmid and a phagemid.

In embodiments using a toxin/antitoxin cell-based system, the method for determining polymerase fidelity comprises filling a gapped plasmid with a polymerase to form a gap-filled plasmid, wherein the gap-filled plasmid comprises a gene encoding a toxin for a cell and a gene encoding an antitoxin and wherein the toxin is functional or non-functional depending on the polymerase fidelity; transforming the gap-filled plasmid into the cell; forming a solution comprising a plurality of transformants and an indicator for detecting the presence of the cell; dividing the solution equally into a first pool and a second pool; forming a plurality of partitions from each of the first and second pools, wherein the first pool comprises an inducer for inducing the expression of the antitoxin; detecting the presence of an antitoxin-neutralized toxin and a mutant toxin in one or more of the partitions from the first pool to determine a total number of transformants and detecting the presence of the mutant toxin in one or more of the partitions from the second pool to determine a number of mutant toxin-containing partitions; subtracting the number of mutant toxin-containing partitions from the total number of transformants to determine a number of wild-type toxin-containing partitions; and determining the fidelity of the polymerase by determining a ratio of the number of mutant toxin-containing partitions to the number of wild-type toxin-containing partitions. In some embodiments, the toxin is CcdB and the antitoxin is CcdA. In some embodiments, the toxin is MazF and the antitoxin is MazE. In certain embodiments, the toxin is HicA and the antitoxin is HicB.

Kits for practicing the subject methods are also provided.

BRIEF DESCRIPTION OF THE DRAWINGS

FIG. 5 shows different aspects of the verification of bacterial growth in droplets as described in Example 3.

FIG. 6 shows different aspects of the functional detection and verification of beta-galactosidase activity in droplets as described in Example 4. FIG. 6B shows background fluorescence from the cells and FIG. 6C shows no fluorescence due to the absence of cells.

FIG. 7 shows different aspects of the determination of beta-galactosidase activity and cells in droplets as described in Example 5.

FIG. 9 shows different aspects of the determination of beta-galactosidase activity and cells in droplets as described in Example 8.

DETAILED DESCRIPTION

Figure 1:
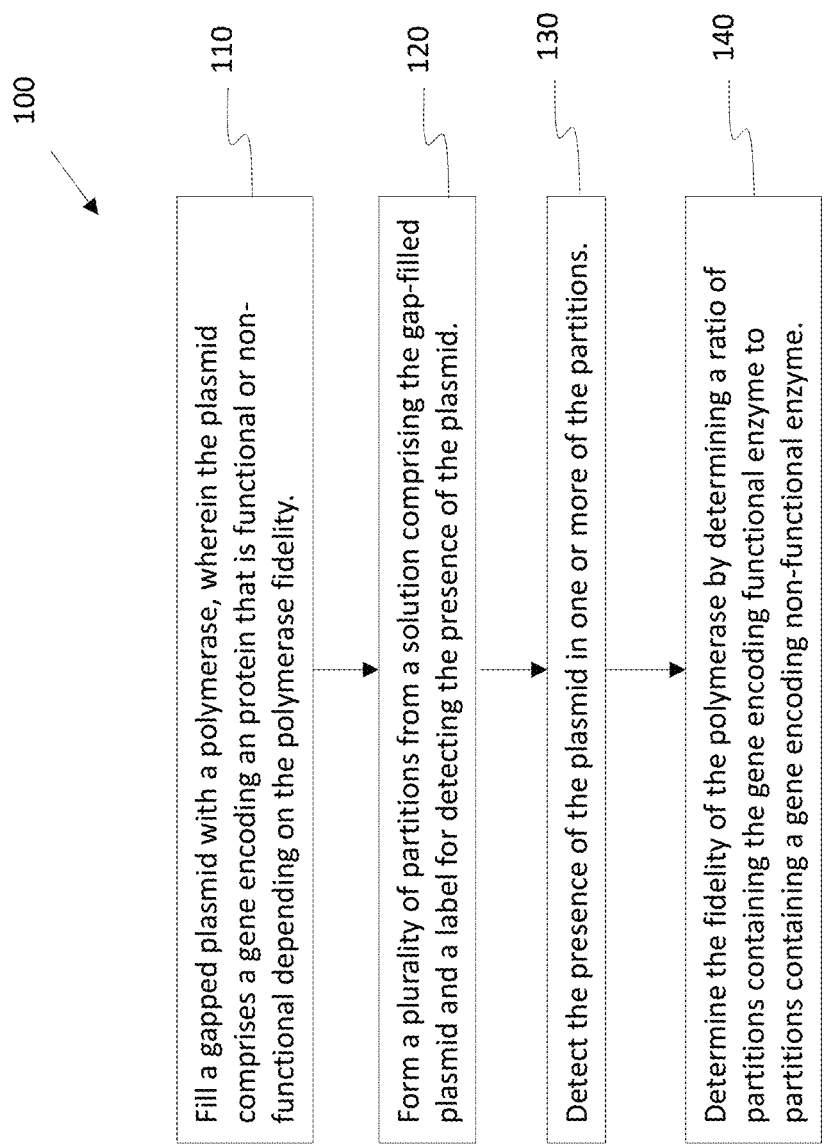
FIG. 1 is a flow chart showing a method of determining polymerase fidelity according to an embodiment of the invention.

Provided herein are methods for determining polymerase fidelity. Methods have been discovered that do not require a blue/colorless colony scoring step. As described herein, the methods are performed in partitions (for example, in droplets in an emulsion).

I. Definitions

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4th ed. 2007); Green et al., MOLECULAR CLONING, A LABORATORY MANUAL (FOURTH EDITION), Cold Spring Harbor Lab Press (Cold Spring Harbor, N.Y. 2012). The term "a" or "an" is intended to mean "one or more." The term "comprise," and variations thereof such as "comprises" and "comprising," when preceding the recitation of a step or an element, are intended to mean that the addition of further steps or elements is optional and not excluded. Any methods, devices and materials similar or equivalent to those described herein can be used in the practice of this invention. The following definitions are provided to facilitate understanding of certain terms used frequently herein and are not meant to limit the scope of the present disclosure.

As used herein, "nucleic acid" means a compound comprising a chain of nucleotide monomers. A nucleic acid may be single-stranded or double-stranded (i.e., base-paired with another nucleic acid), among others. The chain of a nucleic acid may be composed of any suitable number of monomers, such as at least about ten or one hundred, among others. Generally, the length of a nucleic acid chain corresponds to its source, with synthetic nucleic acids (e.g., nucleic acid reagents such as primers and probes) typically being shorter and biologically produced nucleic acids (e.g., nucleic acid analytes) typically being longer.

A nucleic acid can have a natural or artificial structure, or a combination thereof. Nucleic acids with a natural structure, namely, deoxyribonucleic acid (DNA) and ribonucleic acid (RNA), have a backbone of alternating pentose sugar groups and phosphate groups. Each pentose group is linked to a nucleobase (e.g., a purine (such as adenine (A) or guanine (T)) or a pyrimidine (such as cytosine (C), thymine (T), or uracil (U))). Nucleic acids with an artificial structure are analogs of natural nucleic acids and may, for example, be created by changes to the pentose and/or phosphate groups of the natural backbone. Exemplary artificial nucleic acids include glycol nucleic acids (GNA), peptide nucleic acids (PNA), locked nucleic acid (LNA), threose nucleic acids (TNA), and the like.

The sequence of a nucleic acid is defined by the order in which nucleobases are arranged along the backbone. This sequence generally determines the ability of the nucleic acid to bind specifically to a partner chain (or to form an intramolecular duplex) by hydrogen bonding. In particular, adenine pairs with thymine (or uracil) and guanine pairs with cytosine. A nucleic acid that can bind to another nucleic acid in an antiparallel fashion by forming a consecutive string of adenine-thymine and guanine-cytosine base pairs with the other nucleic acid is termed "complementary."

The term "gene" refers to a linear sequence of nucleotides along a segment of DNA that provides the coded instructions for synthesis of RNA, which is translated into a protein.

A "polymerase" refers to an enzyme that performs template (e.g., DNA and/or RNA)-directed (or template-dependent) synthesis of polynucleotides, e.g., DNA and/or RNA. The term encompasses both the full length polypeptide and a domain that has polymerase activity. DNA polymerases are well-known to those skilled in the art, including but not limited to DNA polymerases isolated or derived from *Thermus aquaticus, Pyrococcus furiosus, Thermococcus litoralis,* and *Thermotoga maritime,* or modified versions thereof. Additional examples of commercially available polymerase enzymes include, but are not limited to: Klenow fragment (New England Biolabs® Inc.), Taq DNA polymerase (QIAGEN), 9° N™ DNA polymerase (New England Biolabs® Inc.), Deep Vent™ DNA polymerase (New England Biolabs® Inc.), Manta DNA polymerase (Enzymatics®), Bst DNA polymerase (New England Biolabs® Inc.), and phi29 DNA polymerase (New England Biolabs® Inc.). Polymerases include both DNA-dependent polymerases and RNA-dependent polymerases such as reverse transcriptase. At least five families of DNA-dependent DNA polymerases are known, although most fall into families A, B and C. There is little or no sequence similarity among the various families. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerizing and 3' to 5' exonuclease activity. In *E. coli*, three types of DNA polymerases have been found, DNA polymerases I (family A), II (family B), and III (family C). In eukaryotic cells, three different family B polymerases, DNA polymerases α, δ, and ε, are implicated in nuclear replication, and a family A polymerase, polymerase γ, is used for mitochondrial DNA replication. Other types of DNA polymerases include phage polymerases. Similarly, RNA polymerases typically include eukaryotic RNA polymerases I, II, and III, and bacterial RNA polymerases as well as phage and viral polymerases. RNA polymerases can be DNA-dependent and RNA-dependent.

The term "fidelity" refers to how accurately a DNA polymerase replicates a desired template. Replicating a DNA template involves multiple steps, including the ability to read a template strand, select the appropriate nucleoside triphosphate and insert the correct nucleotide at the 3' primer terminus, such that Watson-Crick base pairing is maintained. In addition to effective discrimination of correct versus incorrect nucleotide incorporation, some DNA polymerases possess a 3'→5' exonuclease activity. This activity, known as "proofreading", is used to excise incorrectly incorporated mononucleotides that are then replaced with the correct nucleotide. High-fidelity PCR utilizes DNA polymerases that couple low misincorporation rates with proofreading activity to give faithful replication of the target DNA of interest.

The terms "label", "detectable label", and "indicator" interchangeably refer to a composition detectable by spectroscopic, photochemical, biochemical, immunochemical, chemical, or other physical means. For example, useful labels include fluorescent dyes (fluorophores), fluorescent quenchers, luminescent agents, electron-dense reagents, enzymes (e.g., that cleave a substrate that is detectable), a fluorescent protein, biotin, digoxigenin, $^{32}P$ and other isotopes, haptens, proteins, nucleic acids, or other substances which may be made detectable, e.g, by incorporating a label into an oligonucleotide, peptide, or antibody specifically reactive with a target molecule. The term includes combinations of single labeling agents, e.g., a combination of fluorophores that provides a unique detectable signature, e.g., at a particular wavelength or combination of wavelengths.

A molecule that is "linked" to a label (e.g., as for a labeled nucleic acid or enzyme as described herein) is one that is bound, either covalently, through a linker or a chemical bond, or noncovalently, through ionic, van der Waals, electrostatic, or hydrogen bonds to a label such that the presence of the molecule may be detected by detecting the presence of the label bound to the molecule.

The term "partitioning" or "partitioned" refers to separating an aqueous solution having one or more of a sample and reactant into a plurality (i.e., more than two) of portions, or "partitions." Partitions can be solid or fluid. In some embodiments, a partition is a solid partition, e.g., a microchannel. In some embodiments, a partition is a fluid partition, e.g., a droplet. In some embodiments, a fluid partition (e.g., a droplet) is a mixture of immiscible fluids (e.g., water and oil). In some embodiments, a fluid partition (e.g., a droplet) is an aqueous droplet that is surrounded by an immiscible carrier fluid (e.g., oil).

II. Methods

Referring to FIG. 1, a method 100 for determining polymerase fidelity will now be described. The steps may be performed in any suitable order, in any suitable combination, and may be combined with or modified by any other suitable aspects of the disclosure provided herein.

A. Gap-Filled Plasmid Formation

In exemplary step 110, a gapped plasmid is filled by a polymerase to form a gap-filled plasmid. A gapped plasmid refers to a plasmid having a single-stranded portion. In some embodiments, the single-stranded portion of the plasmid comprises SEQ ID NO:1 (see Example 5 for listing). The gap-filled plasmid comprises a gene encoding a protein (e.g., an enzyme) that is functional or non-functional depending on the polymerase fidelity. In some embodiments, the gene encoding the enzyme is a lacZα gene and the enzyme is beta-galactosidase. In some embodiments, the enzyme is luciferase or a target specific protease. In some embodiments, the gap-filled plasmid comprises genes encoding a toxin and an antitoxin in a toxin-antitoxin system.

In some embodiments, the toxin-antitoxin system is CcdB-CcdA and the CcdB toxin targets gyrase, which plays a role in DNA replication. The CcdB toxin in this system is functional or non-functional, depending on the polymerase fidelity. In certain embodiments, the toxin-antitoxin system is MazF/MazE and the MazF toxin is functional or non-functional, depending on the polymerase fidelity. In some embodiments, the toxin-antitoxin system is HicA/HicB and the HicA toxin is functional or no-functional, depending on the polymerase fidelity.

B. Partition Formation

In exemplary step 120, a solution comprising a polymerase gap-filled plasmid having a gene encoding a protein is partitioned into a plurality of partitions. In some embodiments, the solution includes a cell having the gap-filled plasmid. In embodiments in which the solution includes a cell, the solution is partitioned at or below 0.15 cells-per-partition (e.g., droplet) to ensure that less than 1% of the partitions carry two or more cells.

In embodiments in which the solution includes a plurality of cells having a gap-filled plasmid encoding a toxin and an antitoxin, the solution having a plurality of transformants is equally divided into a first pool and a second pool and then a plurality of partitions is formed from each of the first and second pools.

In some embodiments, the solution from which the partitions are formed includes a substrate for an enzyme. In embodiments in which the enzyme is beta-galactosidase, exemplary substrates include, but are not limited to, fluorescein di-(beta-D-galactopyranoside), naphthofluorescein di-(beta-D-galactopyranoside), (9H-(1,3-dichloro-9,9-dimethylacridin-2-one-7-yl) beta-D-galactopyranoside), 4-methylumbelliferyl beta-D-gal actopyranoside, and resorufin beta-D-galactopyranoside.

In some embodiments, the gap-filled plasmid includes a label for detecting the presence of the gap-filled plasmid in the partition. Exemplary labels include, but are not limited to, a fluorescent protein encoded by a gene in the plasmid, an enzyme encoded by a gene in the plasmid that cleaves a detectable substrate, a fluorophore (or fluorescent agent), and biotin. Exemplary fluorescent proteins include, but are not limited to, mKO fluorescent protein, green fluorescent protein, cyan fluorescent protein, red fluorescent protein (and red fluorescent protein variants), and yellow fluorescent protein.

Fluorescent agents can include a variety of organic and/or inorganic small molecules and derivatives thereof. For example, fluorescent agents can include but are not limited to cyanines (e.g., Cy™3, Cy™5), phthalocyanines, porphyrins, indocyanines, rhodamines, phenoxazines, phenylxanthenes, phenothiazines, phenoselenazines, fluoresceins (e.g., FAM, FITC, 5-carboxyfluorescein, and 6-carboxyfluorescein), benzoporphyrins, squaraines, dipyrrolo pyrimidones, tetracenes, quinolines, pyrazines, corrins, croconiums, acridones, phenanthridines, rhodamines (e.g., TAMRA, TMR, and Rhodamine Red), pyrene butyrate, acridines, anthraquinones, chalcogenopyrylium analogues, chlorins, naphthalocyanines, methine dyes, indolenium dyes, azo compounds, azulenes, azaazulenes, triphenyl methane dyes, indoles, benzoindoles, indocarbocyanines, benzoindocarbocyanines, BODIPY™ and BODIPY™ derivatives, and analogs thereof. In some embodiments, a fluorescent agent is an Alexa Fluor dye. Fluorescent dyes and fluorescent label reagents include those which are commercially available, e.g., from Invitrogen/Molecular Probes (Eugene, Oreg.) and Pierce Biotechnology, Inc. (Rockford, Ill.). In some embodiments, the label is an intercalating dye. Intercalating dyes include, but are not limited to, SYBR Green and Pico Green (from Molecular Probes, Inc., Eugene, Oreg.), ethidium bromide, propidium iodide, chromomycin, acridine orange, Hoechst 33258, TOTO-I, YOYO-1, and DAPI (4',6-diamidino-2-phenylindole hydrochloride).

In some embodiments, a fluorescent agent is a polymer dot or a quantum dot. The particular quantum dot (QD) employed is not critical to the present invention. Quantum dots are known in the art and are described, for example, by Han et al., "Quantum-dot-tagged Microbeads for Multiplexed Optical Coding of Biomolecules", Nat Biotechnol (July 2001) vol. 19, pp. 631-635. One of skill in the art will appreciate the various quantum dots that may serve as fluorescent labels and that can be employed in embodiments of the invention and which are available from various commercial vendors. Exemplary quantum dots (QDs) include, but are not limited to, the following: cadmium selenide (CdSe) quantum dot nanoparticles (e.g., CdSe Quantum Dot Cores, 480-640 nm emission spectra, Sigma-Aldrich®); cadmium sulfide (CdS) quantum dot nanoparticles (e.g., CdS Quantum Dot Cores, 380-480 nm emission spectra, Sigma-Aldrich®); zinc sulfide-capped cadmium selenide (ZnS-capped CdSe) nanocrystals (e.g., CdSe/ZnS Lumidots™ and CdSe/ZnS NanoDots™, 480-640 nm emission spectra, Sigma-Aldrich®); and cadmium-free quantum dots (e.g., CFQD™, 400-650 nm emission spectra, Sigma-Aldrich®).

In an embodiment, the fluorophore is present in a sufficient amount such that the fluorophore is detectable. In an embodiment, at least 1 fluorophore to 100 fluorophores, 100 fluorophores to 1000 fluorophores, 1000 fluorophores to 10000 fluorophores, 10000 fluorophores to 100000 fluorophores, 100000 fluorophores to 1 million fluorophores, 1 million fluorophores to 10 million fluorophores or at least 10 million fluorophores to 100 million fluorophores are present per partition having a 1 nanoliter volume. In embodiments having a partition volume less than 1 nanoliter, less fluorophores are present per partition (e.g., 1 to 100 fluorophores per 50 femtoliter partition volume).

The gap-filled plasmid can be in a cell-based expression system or in a cell-free expression system. In embodiments in which the expression system is a cell, the gap-filled plasmid can be transformed into a bacterial, a yeast cell, an insect cell, or a mammalian cell. In some embodiments, a bacterial cell, a yeast cell, a mammalian cell, or an insect cell comprises a polymerase gap-filled and nicked plasmid having $a_{lac}$/lacZα gene segment from M13mp2 bacteriophage or a plasmid. In some embodiments, a yeast cell comprises a circular single-stranded DNA derived from reverse transcriptase gap-filled and nicked RNA/DNA hybrid template generated by using single-stranded RNA prepared from MS2 bacteriophage and synthesized single-stranded DNA.

In embodiments having cells, each of the partitions or cells can include an indicator for detecting the presence of the cell. Exemplary indicators include, but are not limited to, a fluorescent protein, an autofluorescent protein, a cell-staining dye, a nuclease alert reagent (e.g, a reagent that is a fluorescence-quenched oligonucleotide probe that emits a fluorescence signal only after nuclease degradation), nuclease activity (e.g., nuclease activity from a nuclease encoded by the plasmid or endogenous nuclease activity from the cell) and antibiotic-resistance (e.g., detectable by turbidity or mass). Exemplary live cell staining dyes include, but are not limited to, carbocyanines (e.g., DiI (DiIC18(3)), DiO (DiOC18(3)), DiD (DiIC18(5)) and DiR (DiIC18(7)) from ThermoFisher), acridine orange, aniline yellow, Bismarck Brown Y, carboxyfluorescein diacetate succinimidyl ester, DiOC6, Green S, methylene blue, neutral red, new methylene blue, Nile blue, Nile red, safranin, FAM™, and HEX™.

In embodiments having a cell-based expression system, the solution from which partitions are formed further includes any components required to grow the cells and express the enzyme encoded by the plasmid in the cell. In some embodiments, the solution comprises culture medium (e.g., Modified Eagle's Medium, Luria broth) and antibiotic to select cells having antibiotic resistance. The solution containing the cells can be incubated at a temperature to grow the cells and to express the enzyme before or after forming the partitions. The incubation temperature used to grow the cells depends on the cell system used and can range from 30° C. to 100° C. In some embodiments using bacterial cells, the incubation temperature used to grow the bacterial cells can be 37° C. In some embodiments using yeast cells, the incubation temperature for growing the yeast cells can be 32° C.

In embodiments having a cell-free expression system, in addition to the gap-filled plasmid, the solution from which partitions are formed can further include components required for in vitro transcription and translation including, but not limited to, a cell extract, an energy source, a supply of amino acids, and cofactors such as magnesium. Exemplary energy sources include, but are not limited to, phosphoenol pyruvate, acetyl phosphate, and creatine phosphate.

Each of the partitions can also include an inducer for inducing the expression of the enzyme encoded by the plasmid. In embodiments in which the enzyme is beta-galactosidase, the inducer can be isopropyl-beta-D-1-thiogalactopyranoside, methyl-beta-D-1-thiogalactopyranoside, lactose or lactose derivatives. In embodiments in which a toxin-antitoxin systems is used, the partitions formed from the first pool include an inducer to induce expression of the antitoxin. In embodiments in which a CcdB/CcdA toxin-antitoxin is expressed by the plasmid, the inducer of CcdA can be tetracycline. In some embodiments, the plasmid encoding the toxin-antitoxin includes a Lac promoter and the inducer is IPTG. In some embodiments, the plasmid encoding the toxin-antitoxin includes an araS promoter and the inducer is arabinose.

The partition can include any of a number of types of partitions, including solid partitions (e.g., wells or tubes) and fluid partitions (e.g., aqueous phase or droplet within an oil phase). In some embodiments, the partitions are droplets. In some embodiments, the partitions are microchannels. Methods and compositions for partitioning a solution are described, for example, in published patent applications WO 2012/135259, WO 2014/117088, WO 2010/036352, and U.S. Pat. No. 9,156,010, the entire content of each of which is incorporated by reference herein.

In some embodiments, a droplet comprises an emulsion composition, i.e., a mixture of immiscible fluids (e.g., water and oil). In some embodiments, a droplet is an aqueous droplet that is surrounded by an immiscible carrier fluid (e.g., oil). In some embodiments, a droplet is an oil droplet that is surrounded by an immiscible carrier fluid (e.g., an aqueous solution). In some embodiments, the droplets described herein are relatively stable and have minimal coalescence between two or more droplets. In some embodiments, less than 0.0001%, 0.0005%, 0.001%, 0.005%, 0.01%, 0.05%, 0.1%, 0.5%, 1%, 2%, 3%, 4%, 5%, 6%, 7%, 8%, 9%, or 10% of droplets generated coalesce with other droplets.

In an embodiment, the droplet is formed by flowing an oil phase through an aqueous phase. The oil for the oil phase may be synthetic or naturally occurring. In some embodiments, the oil comprises carbon and/or silicon. In some embodiments, the oil comprises hydrogen and/or fluorine. Exemplary oils include, but are not limited to, silicone oil, mineral oil, fluorocarbon oil, vegetable oil, or a combination thereof.

The oil phase may comprise a fluorinated base oil which may additionally be stabilized by combination with a fluorinated surfactant such as a perfluorinated polyether. In some embodiments, the base oil comprises one or more of a HFE 7500, FC-40, FC-43, FC-70, or another common fluorinated oil. In some embodiments, the oil phase comprises an anionic fluorosurfactant. In some embodiments, the anionic fluorosurfactant is Ammonium Krytox (Krytox-AS), the ammonium salt of Krytox FSH, or a morpholino derivative of Krytox FSH. Krytox-AS may be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of Krytox-AS is about 1.8%. In some embodiments, the concentration of Krytox-AS is about 1.62%. Morpholino derivative of Krytox FSH may be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of morpholino derivative of Krytox FSH is about 1.8%. In some embodiments, the concentration of morpholino derivative of Krytox FSH is about 1.62%.

In some embodiments, the oil phase further comprises an additive for tuning the oil properties, such as vapor pressure, viscosity, or surface tension. Non-limiting examples include perfluorooctanol and 1H,1H,2H,2H-Perfluorodecanol. In some embodiments, 1H,1H,2H,2H-Perfluorodecanol is added to a concentration of about 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.25%, 1.50%, 1.75%, 2.0%, 2.25%, 2.5%, 2.75%, or 3.0% (w/w). In some embodiments, 1H,1H, 2H,2H-Perfluorodecanol is added to a concentration of about 0.18% (w/w).

In some embodiments, the droplet is formed by flowing an oil phase through an aqueous solution phase having a gap-filled plasmid or a cell with a gap-filled plasmid and one or more components (e.g., reagents) that are used to determine polymerase fidelity. In some embodiments, the one or more components used to determine polymerase fidelity in the aqueous droplet are soluble and/or miscible in water including, but not limited to, one or more salts, buffering agents, reagents (e.g., substrate), surfactants, and/or whatever additional components may be necessary for a desired reaction(s) that may be intended to occur within a formed droplet. All such additional components may be selected to be compatible with the desired reaction or intended assay.

In some embodiments in which the droplet is provided with a buffering agent, a plasmid or a cell and other assay components (e.g., substrate) can be injected into the partition. The plasmid or cell and assay components may be injected into the partition in any order or simultaneously. In some embodiments, a plasmid or cell is injected into the partition followed by a substrate. In certain embodiments, a substrate is injected into the partition followed by a plasmid or cell.

In some embodiments in which a partition is formed from an aqueous phase having a plasmid or cell, a substrate is injected into the partition. In some embodiments in which a partition is formed from an aqueous phase having a substrate, a plasmid or cell is injected into the partition.

Methods of injecting fluids into partitions are described in, for example, WO 2012/135259 and US 2012/0132288, each of which is incorporated by reference in its entirety.

In some embodiments, at least 500 partitions (e.g., droplets), at least 1000 partitions, at least 2000 partitions, at least 3000 partitions, at least 4000 partitions, at least 5000 partitions, at least 6000 partitions, at least 7000 partitions, at least 8000 partitions, at least 10,000 partitions, at least 15,000 partitions, at least 20,000 partitions, at least 30,000 partitions, at least 40,000 partitions, at least 50,000 partitions, at least 60,000 partitions, at least 70,000 partitions, at least 80,000 partitions, at least 90,000 partitions, at least 100,000 partitions, at least 200,000 partitions, at least 300,000 partitions, at least 400,000 partitions, at least 500,000 partitions, at least 600,000 partitions, at least 700,000 partitions, at least 800,000 partitions, at least 900,000 partitions, at least 1,000,000 partitions, at least 2,000,000 partitions, at least 3,000,000 partitions, at least 4,000,000 partitions, at least 5,000,000 partitions, at least 10,000,000 partitions, at least 20,000,000 partitions, at least 30,000,000 partitions, at least 40,000,000 partitions, at least 50,000,000 partitions, at least 60,000,000 partitions, at least 70,000,000 partitions, at least 80,000,000 partitions, at least 90,000,000 partitions, at least 100,000,000 partitions, at least 150,000, 000 partitions, or at least 200,000,000 partitions are formed.

In some embodiments, the droplets that are generated are substantially uniform in shape and/or size. For example, in some embodiments, the droplets are substantially uniform in average diameter. In some embodiments, the droplets that are generated have an average diameter of about 0.001 microns, about 0.005 microns, about 0.01 microns, about 0.05 microns, about 0.1 microns, about 0.5 microns, about 1 microns, about 5 microns, about 10 microns, about 20 microns, about 30 microns, about 40 microns, about 50 microns, about 60 microns, about 70 microns, about 80 microns, about 90 microns, about 100 microns, about 150 microns, about 200 microns, about 300 microns, about 400 microns, about 500 microns, about 600 microns, about 700 microns, about 800 microns, about 900 microns, or about 1000 microns. In some embodiments, the droplets that are generated have an average diameter of less than about 1000 microns, less than about 900 microns, less than about 800 microns, less than about 700 microns, less than about 600 microns, less than about 500 microns, less than about 400 microns, less than about 300 microns, less than about 200 microns, less than about 100 microns, less than about 50 microns, or less than about 25 microns. In some embodiments, the droplets that are generated are non-uniform in shape and/or size.

In some embodiments, the droplets that are generated are substantially uniform in volume. For example, in some embodiments, the droplets that are generated have an average volume of about 0.001 nL, about 0.005 nL, about 0.01 nL, about 0.02 nL, about 0.03 nL, about 0.04 nL, about 0.05 nL, about 0.06 nL, about 0.07 nL, about 0.08 nL, about 0.09 nL, about 0.1 nL, about 0.2 nL, about 0.3 nL, about 0.4 nL, about 0.5 nL, about 0.6 nL, about 0.7 nL, about 0.8 nL, about 0.9 nL, about 1 nL, about 1.5 nL, about 2 nL, about 2.5 nL, about 3 nL, about 3.5 nL, about 4 nL, about 4.5 nL, about 5 nL, about 5.5 nL, about 6 nL, about 6.5 nL, about 7 nL, about 7.5 nL, about 8 nL, about 8.5 nL, about 9 nL, about 9.5 nL, about 10 nL, about 11 nL, about 12 nL, about 13 nL, about 14 nL, about 15 nL, about 16 nL, about 17 nL, about 18 nL, about 19 nL, about 20 nL, about 25 nL, about 30 nL, about 35 nL, about 40 nL, about 45 nL, or about 50 nL.

In some embodiments, the partitions (e.g., droplets) are stable and are capable of long-term storage. In some embodiments, the partitions can be stored at about −70°, −20°, 0°, 3°, 4°, 5°, 6°, 7°, 8°, 9°, 10°, 15°, 20°, 25°, 30°, 35°, or 40° C. for an extended period of time (e.g., for at least 30 days, at least 60 days, at least 90 days, or longer).

Partitions as described herein can contain one or more surfactants to reduce coalescence of droplets during transport. As used herein, a "surfactant" is a surface-active substance capable of reducing the surface tension of a liquid in which it is present. A surfactant, which also or alternatively may be described as a detergent and/or a wetting agent, may incorporate both a hydrophilic portion and a hydrophobic portion, which may collectively confer a dual hydrophilic-hydrophobic character on the surfactant. A surfactant may, in some cases, be characterized according to its hydrophilicity relative to its hydrophobicity. In some embodiments, the aqueous phase incorporates at least one hydrophilic surfactant. The aqueous phase may include at least one nonionic surfactant and/or ionic surfactant. In certain embodiments, the aqueous phase includes a surfactant that is a block copolymer of polypropylene oxide and polyethylene oxide. In some embodiments, the surfactant is a block copolymer of polypropylene oxide and polyethylene oxide sold under the trade names PLURONIC and TETRONIC (BASF). In some embodiments, the surfactant is a nonionic block copolymer of polypropylene oxide and polyethylene oxide sold under the trade name PLURONIC F-68. In some embodiments, the surfactant of the aqueous phase is a water-soluble and/or hydrophilic fluorosurfactant. Exemplary fluorosurfactants for the aqueous phase are sold under the trade name ZONYL (DuPont), such as ZONYL FSN fluorosurfactants. In some cases, the surfactant may include polysorbate 20 (sold under the trade name TWEEN-20 by ICI Americas, Inc.). The concentration of a particular surfactant or total surfactant present in the aqueous phase may be selected to stabilize emulsion droplets prior to heating. In some embodiments, the concentration of surfactant for the aqueous phase is 0.01 to 10%, 0.05 to 5%, 0.1 to 1%, or 0.5% by weight.

C. Detection

In exemplary step 130, the presence of the gap-filled plasmid is detected. In some embodiments, the presence of the gap-filled plasmid is detected by, for example, detecting a signal emitted by the gap-filled plasmid label, by detecting a fluorescent protein encoded by the gap-filled plasmid or by detecting a signal generated by a substrate cleaved by an enzyme encoded by the gap-filled plasmid. In embodiments in which the gap-filled plasmid is in a cell, the presence of the cell is detected by, for example, antibiotic resistance of the cell, by detecting endogenous nuclease activity from the cell, by detecting a fluorescent protein encoded by the gap-filled plasmid or by detecting a signal generated by a substrate cleaved by an enzyme encoded by the gap-filled plasmid.

In embodiments in which a toxin/antitoxin (e.g., CcdB/CcdA) cell-based system is used, the presence of an antitoxin-neutralized toxin and a mutant toxin in one or more of the partitions from the first pool is detected to determine a total number of transformants and the presence of the mutant toxin in one or more of the partitions from the second pool is detected to determine a number of mutant toxin-containing partitions.

In some embodiments, a digital readout assay (e.g., digital analysis) can be used to detect the gap-filled plasmid and/or cell by identifying the partitions containing the gap-filled plasmid label and/or the cell indicator. Generally, the process of digital analysis involves determining for each partition whether the partition is positive or negative for the presence of the label and/or indicator to be detected. A partition is "positive" for the presence of the gap-filled plasmid or cell if a signal from the label or indicator is detected in the partition. A partition is "negative" for the presence of the gap-filled plasmid or cell if no signal is detected in the partition.

In some embodiments, a detector that is capable of detecting a signal or multiple signals is used to analyze each partition for the presence of the gap-filled plasmid and/or cell. For example, in some embodiments, a two-color reader (fluorescence detector) is used. The fraction of positive-counted partitions can be used to determine the fidelity of the polymerase, as will be described in the next section.

D. Fidelity Determination

In exemplary step 140, the polymerase fidelity is determined by determining the ratio of partitions containing the gene encoding functional enzyme to partitions that contain a gene encoding a non-functional enzyme. In some embodiments, the following equation is used to determine the fidelity or error rate of the polymerase (see Fortune J. M., et. al. *J. Biol. Chem.* 2005; 280:29980-29987), $$ER = \frac{\frac{Ni}{N} \times MF}{D \times P} \qquad \text{Eq. 1}$$

Where:

$Ni$=number of a particular type of mutation (e.g., deletion/insertion or base substitution)

$N$=total number of mutations

MF=observed mutation frequency–background mutation frequency

D=number of detectable sites for a particular mutation

P=probability of expressing the mutant lacZα gene (expression frequency)

With Equation 1, the type of mutation (Ni) can be determined only by DNA sequencing of mutant lacZα genes. In the absence of sequencing, Ni/N=1, and the equation can determine only total mutations. The expression frequency for other proteins can be determined empirically.

To determine the fidelity (or error rate) of the polymerase with the toxin/antitoxin system as an example, the number of mutant toxin-containing partitions is subtracted from the total number of transformants to determine a number of wild-type toxin-containing partitions and then a ratio of the number of mutant toxin-containing partitions to the number of wild-type toxin-containing partitions is determined.

III. Kits

In another aspect, kits for determining polymerase fidelity according to the methods described herein are provided. In some embodiments, a kit comprises a plasmid from which a gapped plasmid is formed or a gapped plasmid as described herein. In some embodiments, the gapped plasmid comprises double-stranded DNA or hybrid DNA/RNA. In some embodiments, the kit further comprises a substrate for the enzyme encoded by the plasmid. In some embodiments, the kit further comprises assay components (e.g., buffers, buffer salts, and/or surfactants). In some embodiment, the kit further comprises oil (e.g., silicone oil, mineral oil, fluorocarbon oil, and/or vegetable oil) for making water-in-oil droplets comprising gap-filled plasmid. In some embodiments, the kit further comprises instructions for carrying out the methods described herein.

IV. Systems

Also provided are systems for performing the methods described herein. In some embodiments, the systems include one or more reservoirs comprising reaction components or a plurality of partitions (e.g., droplets) as described herein. In some embodiments, the system further comprises one or more microfluidic channels providing fluid communication between the one or more reservoirs and a detector (s). In some embodiments, all of the above described components are provided as part of a single cartridge. In some embodiments, the cartridge can in turn be inserted into a manifold allowing for attachment to one or more pumps configured to pump the droplets through the microfluidic channels.

In some embodiments, the system further comprises one or more droplet injectors. In some embodiments, the system comprises one or more droplet injectors configured to inject one or more of a sample, binding agent and/or marker into partitions. Droplet injectors are described in, e.g., WO 2012/135259, US 2012/0132288, each of which is incorporated by reference in its entirety.

Exemplary system components are described in, e.g., US2011/0151578, US2011/0218123, US2012/0222748, US2011/0218123, US 2012/0222748, WO2012/135201, WO2012/135259, WO2014/043388, WO 2012/135327.

Detectors as described herein can detect one or both of signals from (i) the plasmid label and/or (ii) the enzyme encoded by the plasmid to determine polymerase fidelity. In some embodiments, the droplets in an emulsion flow through microfluidic channels passing an optical detector that measures a fluorescent signal coming from the droplet.

The spectroscopic intensity and wavelength of the labels and/or indicators may be measured by any methods for spectroscopic analysis known and appreciated by one of ordinary skill in the art. Spectroscopic methods that may be utilized in the present invention include, but are not limited to, a laser and photodetector pair system or more complex optics known to those of skill in the art where the path of an optical beam intersects with the path of a spectroscopic substance and the excitation or illumination of the labels and/or markers is captured by an optical path comprising one or more objectives, mirrors, and/or lenses to direct the light to a photomultiplier tube (PMT) or photosensitive camera. In an embodiment, the fluoroscopy method uses flow cytometry instrumentation. The spectroscopic intensity measurements may comprise one or more methods, including but not limited to, light scatter, absorption, chemiluminescence, fluorescent intensity, radiation decay counts, colorimetric. Partitions to be tested are placed in the path of an excitation energy source such as a light source selected from but is not limited to, lasers, light-emitting diodes (LEDs), arc lamps, broadband light source, and high intensity light bulbs. The label and/or indicator in the partition to be tested scatter, absorb, chemiluminesce, or fluoresce (also referred to herein as "signal") in the form of light at a wavelength substantially different from the wavelength of the light source. This light from the partition to be tested is then captured by a detector or sensor, which may be selected from but is not limited to, a camera, a charge coupled device (CCD), a complementary metal-oxide-semiconductor (CMOS) (alternatively referred to as a complementary-symmetry metal-oxide-semiconductor (COS-MOS)), one or more individual photodiodes, photodiode arrays (PDAs), avalanche photodiodes (APDs), avalanche photodiodes arrays, photomultiplier tubes (PMTs), or photomultiplier tube arrays.

Known optical or electronic means may be optionally used to amplify the light from the light source and/or the light from the sample to be tested and/or to separate one or both into its component wavelengths.

In some, but not all embodiments, all components of the systems and methods described herein are microfluidic. "Microfluidic," as used herein, refers to a device, apparatus or system including at least one fluid channel having a cross-sectional dimension of less than 1 mm, and a ratio of length to largest cross-sectional dimension perpendicular to the channel of at least about 3:1. A "microfluidic channel," as used herein, is a channel meeting these criteria.

Microfluidic systems may be provided that are able to cause two or more droplets to fuse or coalesce into one droplet, for example, in cases where the two or more droplets ordinarily are unable to fuse or coalesce, for example due to composition, surface tension, droplet size, etc. as known to those of ordinary skill in the art. The fluidic droplets may be fused together using any suitable technique, for example, as discussed in U.S. patent application Ser. No. 11/246,911, filed Oct. 7, 2005, entitled "Formation and Control of Fluidic Species," by Link, et al., published as U.S. Patent Application Publication No. 2006/0163385 on Jul. 27, 2006; or U.S. patent application Ser. No. 11/360,845, filed Feb. 23, 2006, entitled "Electronic Control of Fluidic Species," by Link, et al., published as U.S. Patent Application Publication No. 2007/0003442 on Jan. 4, 2007, each incorporated herein by reference. As an example, in microfluidic systems, the surface tension of the droplets, relative to the size of the droplets may prevent fusion or coalescence of the droplets from occurring. In one embodiment, two droplets may be given opposite electrical charges (i.e., positive and negative charges, not necessarily of the same magnitude), which may increase the electrical interaction of the two droplets such that fusion or coalescence of the droplets can occur. Electrical charges (positive or negative) may be imparted onto droplets through the use of Taylor cones, or through any other suitable techniques. For instance, an electric field may be imposed on a reactor containing the droplets, the droplets may be passed through a capacitor, a chemical reaction may occur to cause the droplets to become charged, flowing the droplets over a region with opposite wetting properties, etc.

The "cross-sectional dimension" of the channel is measured perpendicular to the direction of fluid flow. In some embodiments, the fluid channels have maximum cross-sectional dimensions less than about 2 mm, and in some cases, less than about 1 mm. In one set of embodiments, all fluid channels are microfluidic or have a largest cross sectional dimension of no more than about 2 mm or about 1 mm. In certain embodiments, the fluid channels may be formed in part by a single component (e.g. an etched substrate or molded unit). Larger channels, tubes, chambers, reservoirs, etc. can be used to store fluids in bulk and to deliver fluids to components of the invention. In some embodiments, the maximum cross-sectional dimension of the channels) containing embodiments of the invention are less than about 500 microns, less than about 200 microns, less than about 100 microns, less than about 50 microns, or less than about 25 microns.

A "channel," as used herein, means a feature on or in an article (substrate) that at least partially directs the flow of a fluid. The channel can have any cross-sectional shape (circular, oval, triangular, irregular, square or rectangular, or the like) and can be covered or uncovered. In embodiments where it is completely covered, at least one portion of the channel can have a cross-section that is completely enclosed, or the entire channel may be completely enclosed along its entire length with the exception of its inlet(s) and outlet(s). A channel may also have an aspect ratio (length to average cross sectional dimension) of at least about 2:1, more typically at least about 3:1, at least about 5:1, or at least about 10:1 or more. An open channel generally will include characteristics that facilitate control over fluid transport, e.g., structural characteristics (an elongated indentation) and/or physical or chemical characteristics (hydrophobicity vs. hydrophilicity) or other characteristics that can exert a force (e.g., a containing force) on a fluid. The fluid within the channel may partially or completely fill the channel. In some cases where an open channel is used, the fluid may be held within the channel, for example, using surface tension (i.e., a concave or convex meniscus).

The channel may be of any size, for example, having a largest dimension perpendicular to fluid flow of less than about 5 mm or about 2 mm, or less than about 1 mm, or less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 nm, or less than about 10 nm. In some cases the dimensions of the channel may be chosen such that fluid is able to freely flow through the article or substrate. The dimensions of the channel may also be chosen, for example, to allow a certain volumetric or linear flowrate of fluid in the channel. Of course, the number of channels and the shape of the channels can be varied by any method known to those of ordinary skill in the art. In some cases, more than one channel or capillary may be used. For example, two or more channels may be used, where they are positioned inside each other, positioned adjacent to each other, positioned to intersect with each other, etc.

Non-limiting examples of microfluidic systems that may be used with the present invention are disclosed in U.S. patent application Ser. No. 11/246,911, filed Oct. 7, 2005, entitled "Formation and Control of Fluidic Species," published as U.S. Patent Application Publication No. 2006/0163385 on Jul. 27, 2006; U.S. patent application Ser. No. 11/024,228, filed Dec. 28, 2004, entitled "Method and Apparatus for Fluid Dispersion," published as U.S. Patent Application Publication No. 2005/0172476 on Aug. 11, 2005; U.S. patent application Ser. No. 11/360,845, filed Feb. 23, 2006, entitled "Electronic Control of Fluidic Species," published as U.S. Patent Application Publication No. 2007/000342 on Jan. 4, 2007; International Patent Application No. PCT/US2006/007772, filed Mar. 3, 2006, entitled "Method and Apparatus for Forming Multiple Emulsions," published as WO 2006/096571 on Sep. 14, 2006; U.S. patent application Ser. No. 11/368,263, filed Mar. 3, 2006, entitled "Systems and Methods of Forming Particles," published as U.S. Patent Application Publication No. 2007/0054119 on Mar. 8, 2007; U.S. Provisional Patent Application Ser. No. 60/920,574, filed Mar. 28, 2007, entitled "Multiple Emulsions and Techniques for Formation"; and International Patent Application No. PCT/US2006/001938, filed Jan. 20, 2006, entitled "Systems and Methods for Forming Fluidic proplets Encapsulated in Particles Such as Colloidal Particles," published as WO 2006/078841 on Jul. 27, 2006, each incorporated herein by reference in their entireties.

Computer Implemented Methods and Systems

Any of the methods described herein may be totally or partially performed with a computer system including one or more processors, which can be configured to perform the steps of the methods. Thus, embodiments can be directed to computer systems configured to perform the steps of any of the methods described herein, potentially with different components performing a respective step or a respective group of steps. Although presented as numbered or ordered steps, steps of the methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

In some embodiments, the computer implemented method is implemented by a computer system that is in electronic communication with a detector that is capable of detecting a signal emitted from a partition in a channel of a microfluidic device or in an image of a microfluidic device.

The disclosure further provides a computer product that is capable of performing any one of or all of the steps of the methods described herein. Thus, in some embodiments, the computer product comprises a non-transitory computer readable medium storing a plurality of instructions for controlling a processor to perform an operation of one or more of the method steps described herein.

Figure 2:
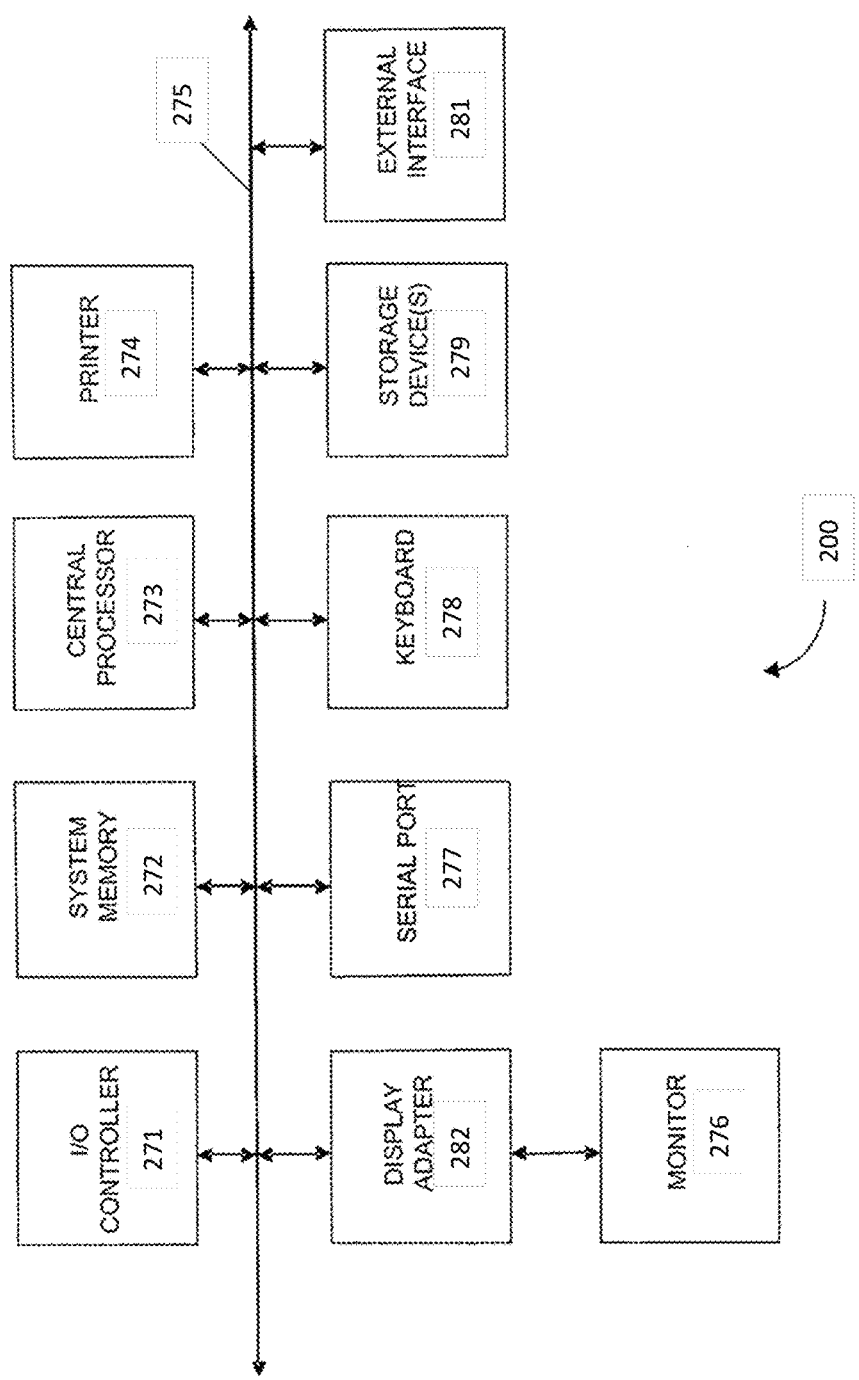
FIG. 2 shows a block diagram of an example computer system usable with the methods and systems according to embodiments of the invention.

FIG. 2 shows a block diagram of an example computer system 200 usable with methods and system according to embodiments of the invention.

Any of the computer systems mentioned herein may utilize any suitable number of subsystems. Examples of such subsystems are shown in FIG. 2 in computer apparatus 200. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 2 are interconnected via a system bus 275. Additional subsystems such as a printer 274, a keyboard 278, a storage device(s) 279, a monitor 276, which is coupled to a display adapter 282, and others are shown. Peripherals and input/output (I/O) devices, which couple to I/O controller 271, can be connected to the computer system by any number of means known in the art, such as a serial port 277. For example, the serial port 277 or an external interface 281 (e.g. Ethernet, Wi-Fi, etc.) can be used to connect the computer system 200 to a wide area network such as the Internet, a mouse input device, or a scanner. The interconnection via the system bus 275 allows the central processor 273 to communicate with each subsystem and to control the execution of instructions from the system memory 272 or the storage device(s) 279 (e.g., a fixed disk, such as a hard drive or optical disk), as well as the exchange of information between subsystems. The system memory 272 and/or the storage device(s) 279 may embody a computer readable medium. Any of the data mentioned herein can be output from one component to another component and can be output to the user.

A computer system can include a plurality of the same components or subsystems, e.g., connected together by the external interface 281 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that the embodiments described above can be implemented in the form of control logic using hardware (e.g. an application specific integrated circuit or field programmable gate array) and/or using computer software with a generally programmable processor in a modular or integrated manner. As used herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments described herein using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present disclosure may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

EXAMPLES

The following examples are provided by way of illustration only and not by way of limitation. Those of skill in the art will readily recognize a variety of non-critical parameters that could be changed or modified to yield essentially the same or similar results.

Example 1—Scheme 1 for Determining Polymerase Fidelity

Figure 3:
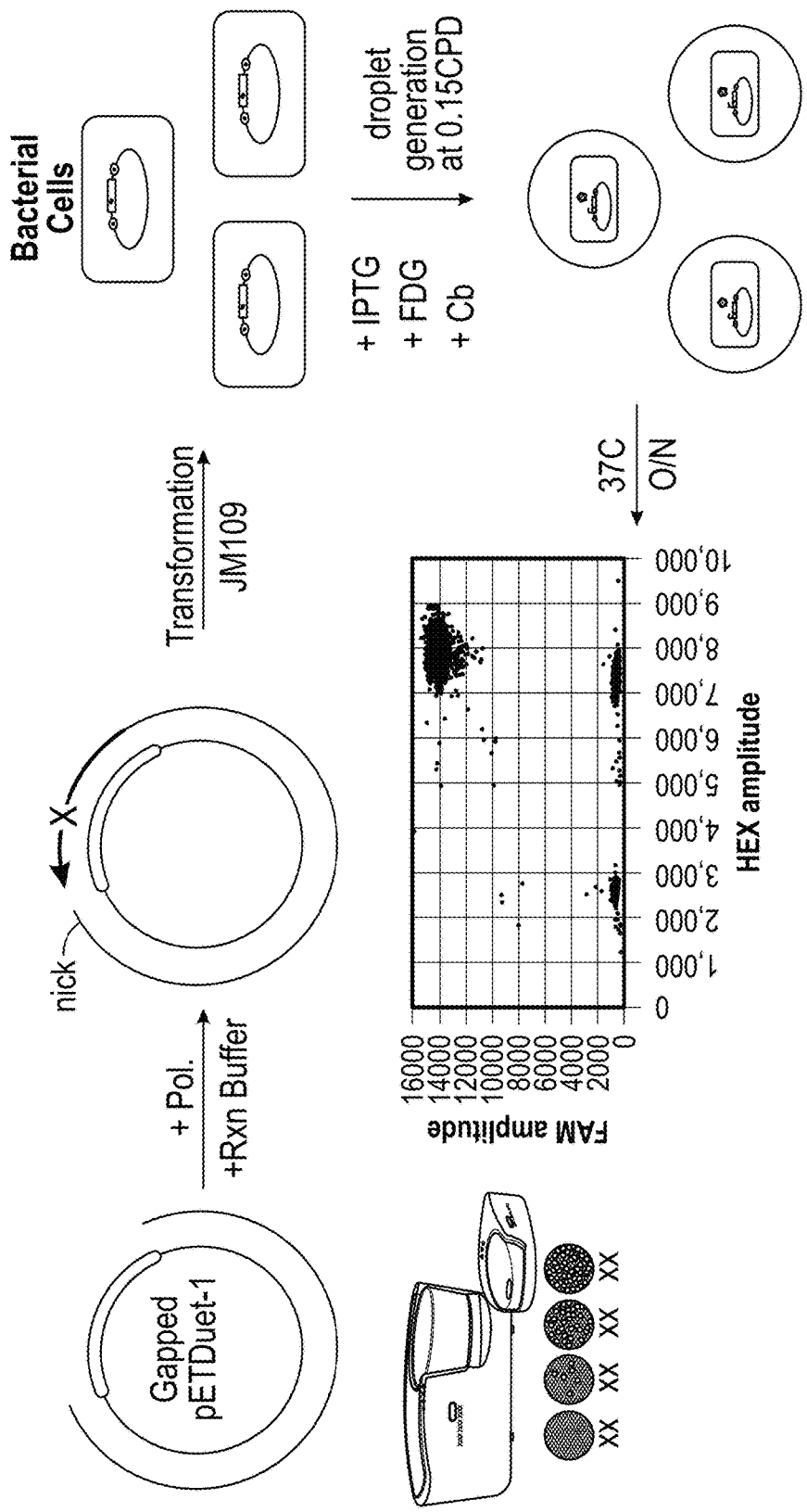
FIG. 3 depicts "Scheme 1" for determining polymerase fidelity (e.g., DNA polymerase fidelity) as described in Example 1.

This example illustrates a method of determining DNA polymerase fidelity. In this scheme (see FIG. 3), gapped DNA template is prepared based on a modified plasmid-based gapped DNA preparation process as described in Keith B. J., Jozwiakowski S. K., and Connolly B. A. *Anal. Biochem.* 2013 Feb. 15; 433(2): 153-161. The gapped plasmid has a gene encoding beta-galactosidase for determining DNA polymerase fidelity and mKO fluorescent protein for detecting the presence of a cell in a partition. After gap filling the plasmid with DNA polymerase, nicked plasmid is transformed into competent bacterial cells. Partitions are formed from a solution containing the bacterial cells and components (e.g., beta-galactosidase inducer and substrate, culture medium with low fluorescence) needed for beta-galactosidase and mKO fluorescent protein expression and detection. The ratio of cells to partitions is adjusted according to Poisson distribution so that each partition contains either one cell or no cells. The partitions are incubated overnight at 37° C. to allow cell growth and protein expression. The next day, when each of the partitions is exposed to light, if present, the cleaved beta-galactosidase substrate and the mKO fluorescent protein emit a fluorescent signal. Empty and cell-containing partitions are determined as are partitions having functional versus nonfunctional beta-galactosidase. The ratio of functional versus nonfunctional beta-galactosidase partitions among cell-containing partitions is used to determine the DNA polymerase fidelity.

Example 2—Scheme 2 for Determining Polymerase Fidelity

Figure 4:
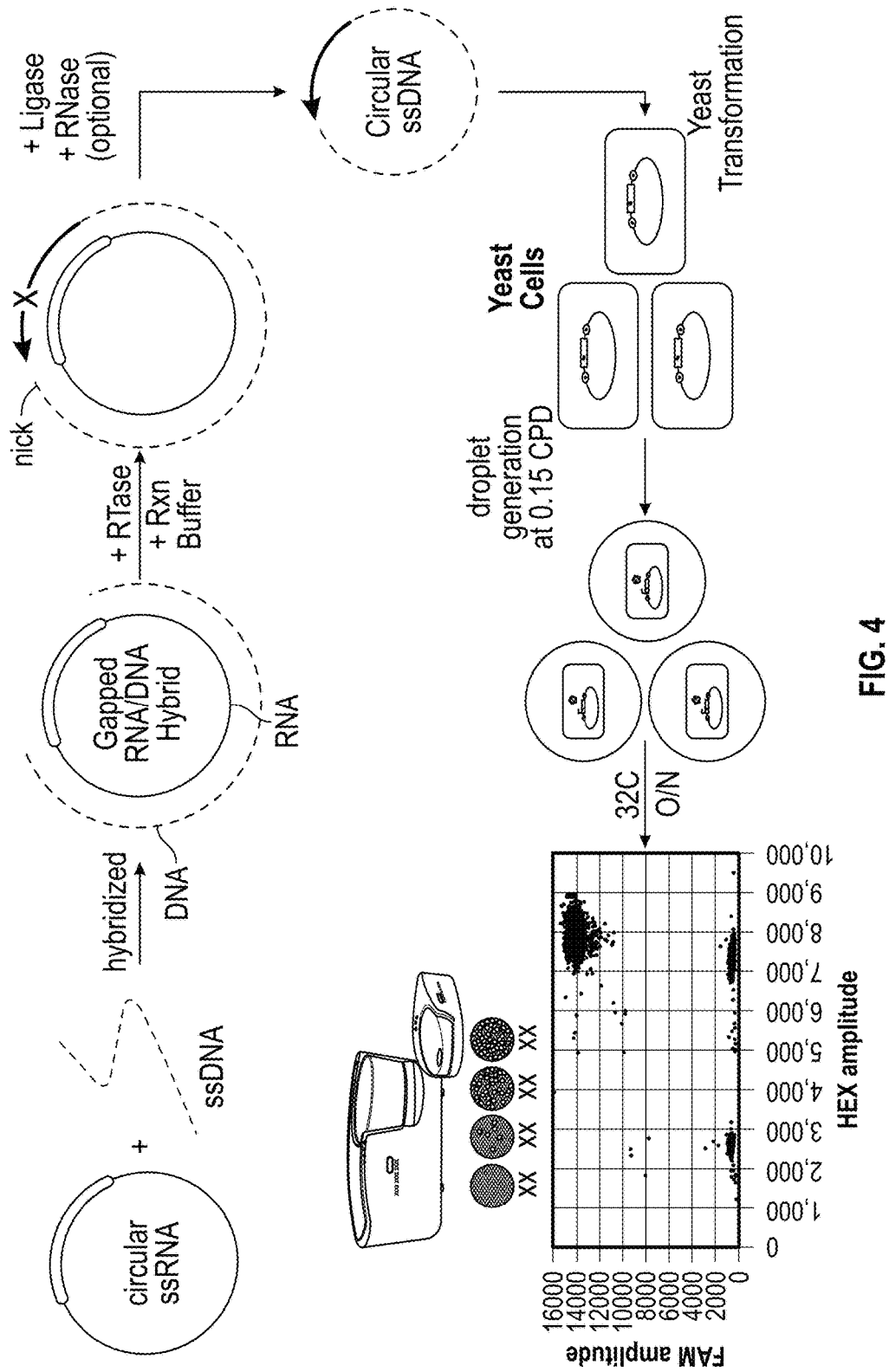
FIG. 4 depicts "Scheme 2" for determining polymerase fidelity (e.g., reverse transcriptase fidelity) as described in Example 2.

This example illustrates a method of determining reverse transcriptase fidelity. According to this scheme (see FIG. 4), gapped RNA/DNA hybrid template is generated by using single-stranded RNA prepared from MS2 bacteriophage and synthesized single-stranded DNA. The gapped plasmid has a gene encoding beta-galactosidase for determining reverse transcriptase fidelity and mKO fluorescent protein for detecting the presence of a cell in a partition. After gap filling the plasmid with reverse transcriptase, nicked hybrid plasmid is transformed into yeast cells. Partitions are formed from a solution containing the yeast cells and components (e.g., beta-galactosidase inducer and substrate) needed for beta-galactosidase and mKO fluorescent protein expression and detection. The ratio of cells to partitions is adjusted according to Poisson distribution so that each partition contains either one cell or no cells. The partitions are incubated overnight at 32° C. to allow cell growth and protein expression. The next day, when each of the partitions is exposed to light, if present, the cleaved beta-galactosidase substrate and the mKO fluorescent protein emit a fluorescent signal. Empty and cell-containing partitions are determined as are partitions having functional versus nonfunctional beta-galactosidase. The ratio of functional versus nonfunctional beta-galactosidase partitions among cell-containing partitions is used to determine reverse transcriptase fidelity.

Example 3—Verification of Bacterial Cell Growth in Droplets

Figure 5B:
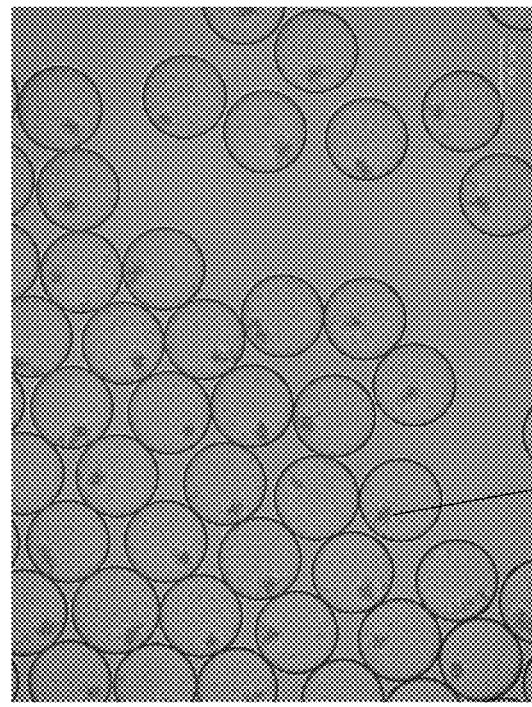
FIG. 5A shows no bacterial cells in droplets and FIG. 5B shows cell growth in droplets.
Figure 5A:
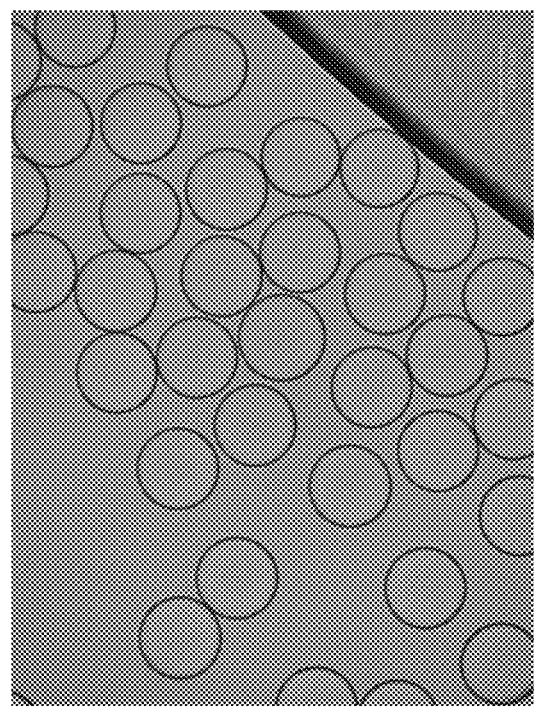

This example illustrates the growth of cells in a droplet system. Water-in-oil drops with or without JM109 bacterial cells were incubated at 37° C. degree overnight. The next day, colonies of bacterial cells were observed under microscope as indicated by the arrow in FIG. 5B. FIG. 5A shows droplets with no bacterial cells.

Figure 6A:
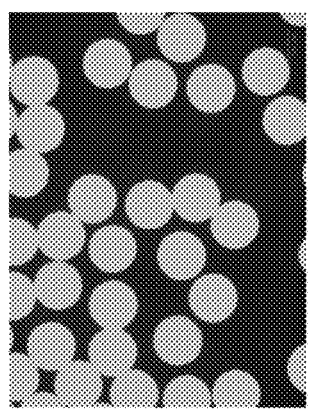
FIGS. 6A and 6D show droplets with JM109 cells transformed with pUC19.
Figure 6B:
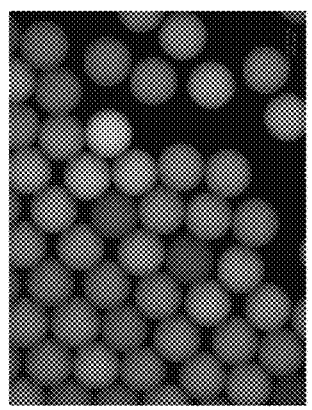
FIGS. 6B and 6E show droplets with JM109 cells transformed with pET11.
Figure 6C:
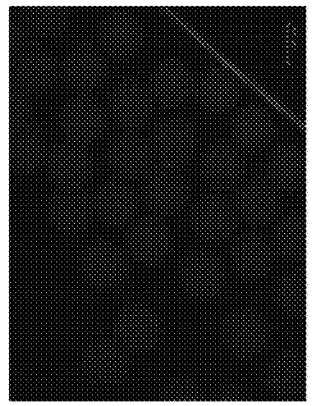
FIGS. 6C and 6F show droplets with no cells.
Figure 6D:
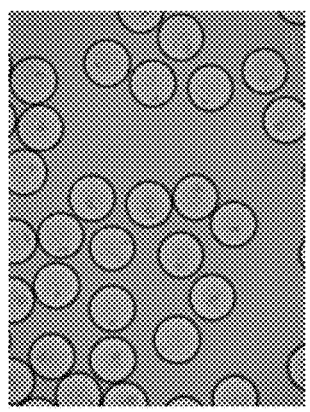
Figure 6E:
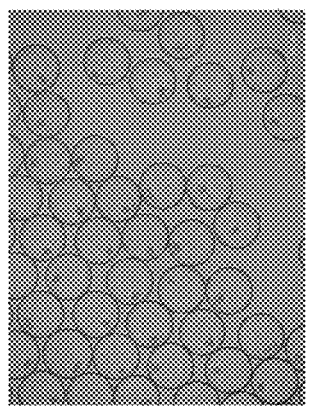
Figure 6F:
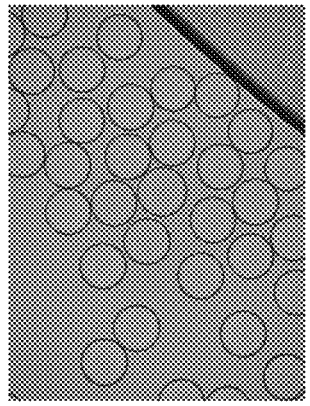

Example 4—Functional Detection and Verification of Beta-Galactosidase Activity in Droplets This example illustrates the detection and verification of beta-galactosidase activity in water-in-oil droplets. JM109 bacterial cells were transformed with plasmids pUC19 or pET11 separately. The pUC19 plasmid contains LacZ α-peptide and is compatible with beta-galactosidase alpha-complementation system. The pET11 plasmid served as a negative control. After transformation, transformants were partitioned by using a water-in-oil droplet system in the presence of Fluorescein Di-β-D-Galactopyranoside (FDG) and inducer Isopropyl β-D-1-thiogalactopyranoside (IPTG). Bio-Rad QX200™ Droplet Generation Oil for EvaGreen (Cat #1864005) was used to make the water-in-oil droplets. Transformant containing droplets were incubated at 37° C. degree overnight to allow cell growth, protein expression, and substrate cleavage. Upon substrate cleavage, FDG was converted by galactosidase into galactose and fluorescein, which has a green fluorescence, was detected under a fluorescent microscope as shown in FIG. 6A. FIGS. 6A and 6D show droplets with JM109 cells transformed with pUC19, FIGS. 6B and 6E show droplets with JM109 cells transformed with pET11, and FIGS. 6C and 6F show droplets with no cells. FIG. 6B shows background fluorescence from the cells and FIG. 6C shows no fluorescence due to the absence of cells.

Example 5—Detection of Beta-Galactosidase Activity and Cells in Droplets Using a Nuclease-Sensitive Oligo Substrate for HEX This example illustrates the detection of beta-galactosidase activity and the presence of cells in droplets. The following gene segment of the lac operon and lacZ alpha fragment was cloned into a dual expression vector (e.g., pETDuet-1, Novagen) at the Cla-1 and AfI-II restriction enzyme sites:

```
Cla-I (ATCGAT)
                                           SEQ ID NO: 1
ATCGATccTcAGCGCAACGCAATTAATGTGAGTTAGCTCACTCATTAGGC

ACCCCAGGCTTTACACTTTATGCTTCCGGCTCGTATGTTGTGTGGAATTG
```

```
                            -continued
TGAGCGGATAACAATTTCACACAGGAAACAGCTATGACCATGATTACGAA

TTCACTGGCCGTCGTTTTACAACGTCGTGACTGGGAAAACCCTGGCGTTA

CCCAACTTAATCGCCTTGCAGCACATCCCCCTTTCGCCAGCTGGCGTAAT

AGCGAAGAGGCCCGCACCGAcCGCCCTTCCCAACAGTTGCGCAGCCTcAg cGGCGAATGGCGCTTTGCCTGGTTTCCGGCACCAGAAGCGGTGCCGGAAA

GCTGGCTGGAGTGCGATCTTCCTGAGGCCGATACGGTCGTCGTCCCCTCA

AACTGGCAGATGCACGGTTACGATGCGCCCATCTACACCAACGTAACCTA

TCCCATTACGGTCAATCCGCCGTTTGTTCCCACGGAGAATCCGACGGGTT

GTTACTCGCTCACATTTAATGTTGATGAAAGCTGGCTACAGGAAGGCCAG

ACGCGAATTATTTTTGATGGCGTTCCTATTGGTTAATGCTTAAG

AfI-II (CTTAAG)
```

After transformation of the plasmid into JM109 bacterial cells, transformants were partitioned by using a water-in-oil droplet system in the presence of FDG, a HEX/Quencher-labeled nucleic acid (substrate of nuclease), IPTG, and carbenicillin (antibiotic). Bio-Rad QX200™ Droplet Generation Oil for EvaGreen (Cat #1864005) was used to the make water-in-oil droplets. Transformant containing droplets were then incubated at 37° C. degrees overnight to allow cell growth, protein expression, and substrate cleavage.

Figure 7A:
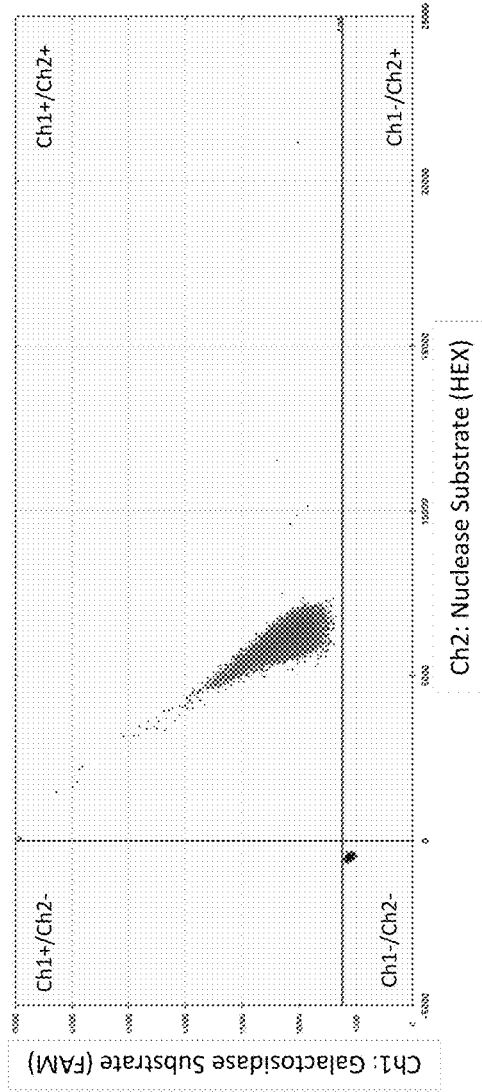
FIG. 7A is a plot of the signal from the cleaved beta-galactosidase substrate (e.g., FAM signal; Y-axis) versus the signal from the cleaved nuclease substrate (e.g., HEX signal; X-axis).
Figure 7B:
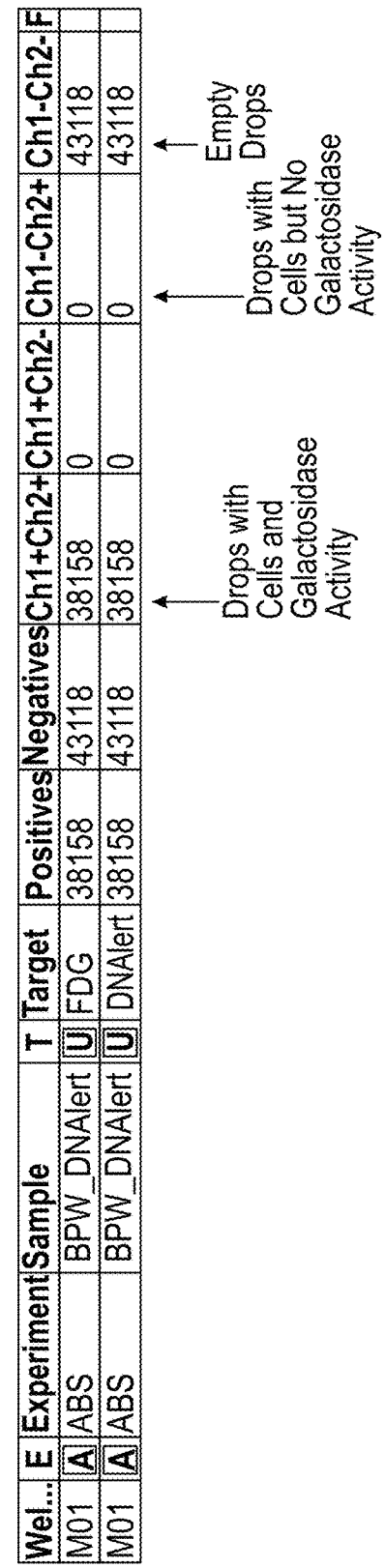
FIG. 7B is a table of the number of droplets having a FAM (Ch1) fluorescent signal and/or a HEX (Ch2) fluorescent signal.

After overnight incubation, the presence of FAM (Ch1) and HEX (Ch2) fluorescent signals within each drop was detected by using a Bio-Rad QX200 droplet reader. FIG. 7A is a plot of the signal from the cleaved beta-galactosidase substrate (e.g., FAM signal; Y-axis) versus the signal from the cleaved nuclease substrate (e.g., HEX signal; X-axis). FIG. 7A shows the detection of two distinct drop populations: empty drops and drops with cells having functional galactosidase activity. In FIG. 7A, the growth of bacterial cells in the presence of antibiotics resulted in release of endogenous bacterial nucleases, which in turn cleaved the HEX/Quencher-labeled nucleic acid oligo and generated a HEX signal (X-axis). In addition, expression of functional beta galactosidase within the cells cleaved substrate FDG and generated a FAM signal (Y-axis). As a result, a droplet population with no FAM and HEX signals indicated empty droplets (Ch1−/Ch2− of FIG. 7B). In contrast, a droplet population with both FAM and HEX signals (Ch1+/Ch2+ of FIG. 7B) suggested the presence of live bacterial cells and functional beta-galactosidase activity.

Example 6—Determination of Polymerase Fidelity

This example illustrates the determination of polymerase fidelity according to the invention.

The dual expression vector of Example 5 is used to produce gapped plasmid by using a method as described in Keith B. J., Jozwiakowski S. K., and Connolly B. A. *Anal. Biochem.* 2013 Feb. 15; 433(2): 153-161. In brief, a segment of double-stranded plasmid that carries lac operon and lacZ alpha is flanked by two single-strand nicking endonuclease sites. The presence of nicking sites allows one of the duplex strands to be cut, and later the cut strand is removed in the presence of complementary competitor DNA. Purified gapped plasmid containing lac operon and lacZ alpha reporter gene fragment in a single-strand region is used to determine the error rate of polymerase in polymerization process. The entire process is collectively called polymerase fidelity test.

During the polymerase fidelity test, gapped plasmids are incubated with target polymerase at the desired temperature for that polymerase. The free 3' end of the gapped plasmid serves as an initiation point, while the single-stand region of the gapped plasmid acts as the template of polymerization. After polymerization, single-nicked plasmids are created, and are transformed into JM109 bacterial cells. JM109 transformants are next partitioned by using water-in-oil droplet system at or below 0.15 cell-per-drop (CPD) level to ensure less than 1% of drops that carry 2 or more cells. In addition to nicked plasmid, each partition also contains Fluorescein Di-D-Galactopyranoside (FDG, substrate of beta galactosidase), HEX/Quencher-labeled nucleic acid oligo (substrate of nuclease), lactose (an inducer of protein expression), and carbencillin (antibiotic). Transformant containing drops are then incubated at 37° C. degrees overnight to allow cell growth, protein expression, and substrate cleavage.

After overnight incubation, the presence of FAM (Ch1) and HEX (Ch2) fluorescent signals within each drop are detected by using the Bio-Rad QX200 droplet reader. As in the previous example, the presence of live bacterial cells is detected by the HEX signal and the expression of functional beta galactosidase within the cells is detected by the FAM signal. Droplets with no FAM and HEX signals indicated empty drops (e.g., Ch1−/Ch2− as in FIG. 7B). Droplets with both FAM and HEX signal (e.g., Ch1+/Ch2+ as in FIG. 7B) indicate the presence of live bacterial cells and functional beta-galactosidase activity. Droplets having only a HEX signal indicate a mutation in the lacZ alpha fragment (e.g., Ch1−/Ch2+ as in FIG. 7B) introduced by polymerase during polymerization. The error rate of polymerization is then determined by calculating the ratio of mutant to non-mutant droplet population.

Example 7—Determination of Polymerase Fidelity—Toxin/Antitoxin System

This example illustrates the determination of DNA polymerase fidelity according to the invention using CcdA/CCdB Type II toxin-antitoxin system within cells in droplets. CcdB is the toxin from the ccd system on the *E. coli* F plasmid and acts as a gyrase poison. CcdA is an antidote that interacts with CcdB to neutralize its toxicity. The plasmid that contains the CcdA/CCdB Type II toxin-antitoxin system is used to produce gapped plasmid by using a method as described in Keith B. J., Jozwiakowski S. K., and Connolly B. A. Anal. Biochem. 2013 Feb. 15; 433(2): 153-161. In brief, the expression of CcdA is placed under the control of a specific inducer (e.g. IPTG or tetracycline). In contrast, CcdB is constitutively expressed in this system. A segment of double-stranded plasmid that carries CcdB gene is flanked by two single-strand nicking endonuclease sites. The presence of nicking sites allows one of the duplex strands to be cut, and later the cut strand is removed in the presence of complementary competitor DNA. Purified gapped plasmid with the CcdB gene fragment in a single-strand region is used to determine the error rate of polymerase in polymerization process.

During the polymerase fidelity test, gapped plasmids are incubated with target polymerase at the desired temperature for that polymerase. The free 3' end of the gapped plasmid serves as an initiation point, while the single-stand region of the gapped plasmid acts as the template of polymerization. After polymerization, single-nicked plasmids are created and then transformed into bacterial cells. Transformants are next separated into two equal portions, pool-A and pool-B, and then are partitioned with HEX/Quencher-labeled nucleic acid oligo (substrate of nuclease), antibiotics, and inducer (pool-A only) by using a water-in-oil droplet system at or below 0.15 cell-per-drop (CPD) level that ensures less than 1% of drops that carry 2 or more cells (see FIG. 8). Droplets are incubated at 37° C. degrees overnight to allow cell growth and protein expression. After overnight incubation, the presence of HEX fluorescent signals within each drop are detected by using the Bio-Rad QX200 droplet reader.

Figure 8:
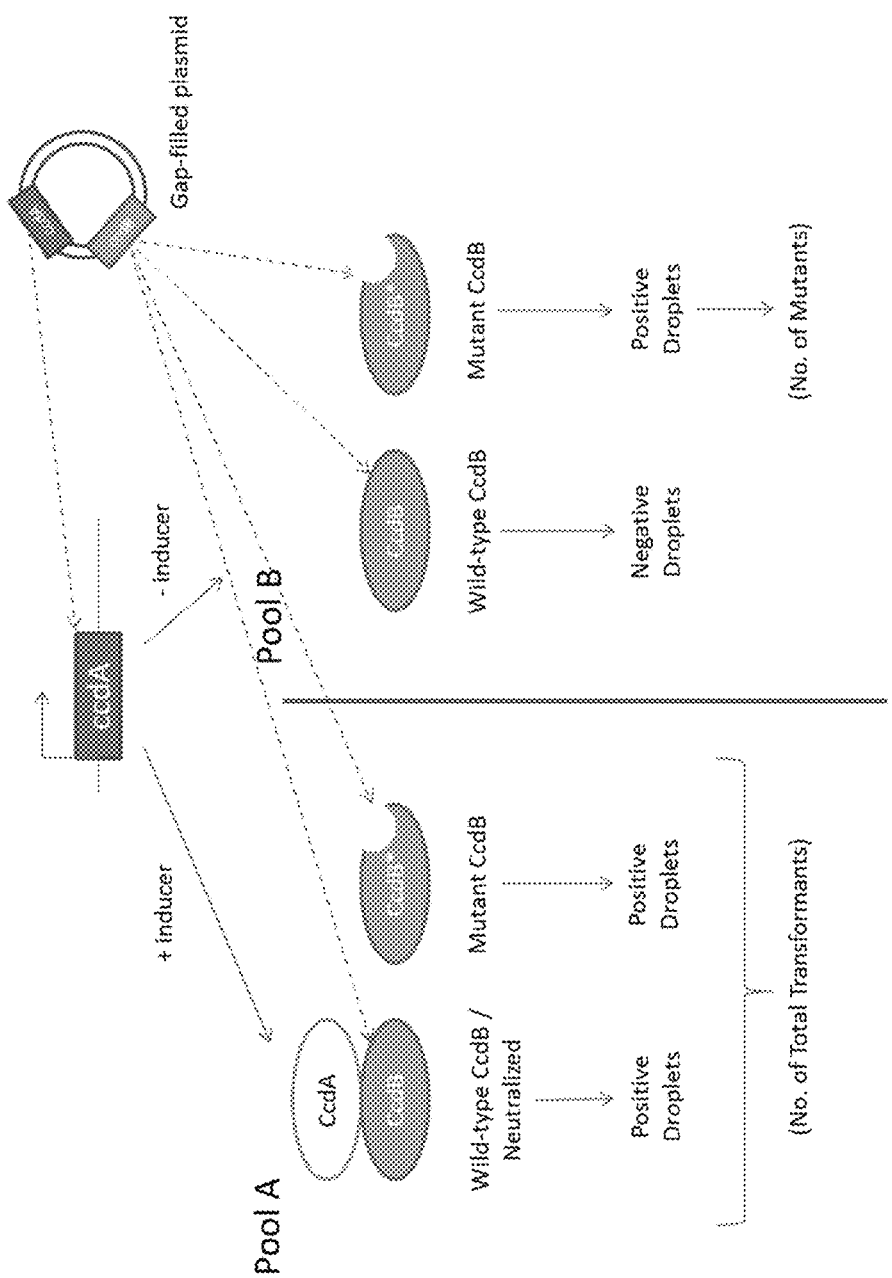
FIG. 8 depicts "Scheme 3" for determining polymerase fidelity as described in Example 7.

As illustrated in FIG. 8, in the presence of the specific inducer (e.g. IPTG or tetracycline), expression of CcdA neutralizes wild-type CcdB toxicity, while mutant CcdB (generated during polymerization) remains non-functional. Together they results in cell growth within droplets. Therefore, the HEX positive population of pool A indicates the total number of transformant. Droplets with no HEX signals indicate empty drops. In contrast, the HEX positive population of pool B indicates the total number of mutants generated during polymerization. As a result, subtraction of the number of positive drops in pool A with pool B gives the number of wild-type CcdB. The error rate of polymerization can be determined by calculating the ratio of mutant to wild-type droplet population in pool B.

Example 8—Detection of Beta-Galactosidase Activity and Cells in Droplets Using a Dye Substrate for HEX This example illustrates the detection of beta-galactosidase activity and the presence of cells in droplets. The transformants from Example 5 were partitioned by using a water-in-oil droplet system in the presence of FDG, C12-resazurin (dye substrate for HEX), IPTG, and carbenicillin (antibiotic). Bio-Rad QX200™ Droplet Generation Oil for EvaGreen (Cat #1864005) was used to make the water-in-oil droplets. Transformant containing droplets were then incubated at 37° C. degrees overnight to allow cell growth, protein expression, and substrate cleavage.

Figures 9A, 9B:
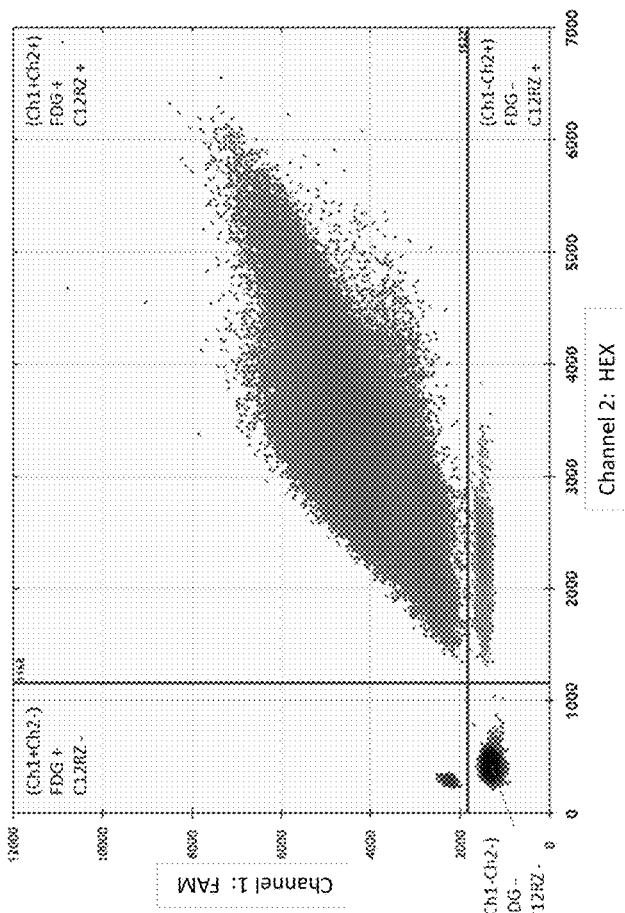
FIG. 9A is a plot of the signal from the cleaved beta-galactosidase substrate (e.g., FAM signal; Y-axis) versus the signal from C12-resazurin substrate (e.g., HEX signal; X-axis).
FIG. 9B is a table of the number of droplets having a FAM (Ch1) fluorescent signal and/or a HEX (Ch2) fluorescent signal.

After overnight incubation, the presence of FAM (Ch1) and HEX (Ch2) fluorescent signals within each drop was detected by using a Bio-Rad QX200 droplet reader. FIG. 9A is a plot of the signal from the cleaved beta-galactosidase substrate (e.g., FAM signal; Y-axis) versus the signal from the cleaved HEX substrate (e.g., HEX signal; X-axis). FIG. 9A shows the detection of four distinct drop populations: empty droplets, droplets with cells having functional galactosidase activity, droplets with cells having both galactosidase and HEX activity, and droplets with cells having functional HEX activity. In FIG. 9A, the growth of bacterial cells in the presence of antibiotics resulted in reduction of resazurin to resorufin which generated a HEX signal (X-axis). In addition, expression of functional beta galactosidase within the cells cleaved substrate FDG and generated a FAM signal (Y-axis). As a result, a droplet population with no FAM and HEX signals indicated empty droplets (Ch1−/Ch2− of FIG. 9B). In contrast, a droplet population with both FAM and HEX signals (Ch1+/Ch2+ of FIG. 9B) suggested the presence of live bacterial cells and functional beta-galactosidase activity.

All patents, patent applications, and other published reference materials cited in this specification are hereby incorporated herein by reference in their entirety.

What is claimed is:

1. A method for determining a polymerase fidelity, the method comprising:
   (a) filling a gapped plasmid with a polymerase to form a gap-filled plasmid, wherein the gap-filled plasmid comprises a first gene encoding a protein that is functional or non-functional depending on the polymerase fidelity and a second gene encoding a protein for detecting the presence of a host cell in a partition in step (d),
   (b) transforming a host cell with the gap-filled plasmid;
   (c) forming a plurality of partitions from a solution comprising the host cell, wherein the plurality of partitions is a plurality of droplets comprising cell culture medium, and wherein the droplets are incubated under conditions that promote protein expression in the host cell;
   (d) detecting the presence of a transformed host cell in one or more of the partitions;
   (e) detecting the presence or absence of the functional protein in one or more of the partitions; and
   (f) determining the polymerase fidelity by determining a ratio of partitions containing the functional protein to partitions containing a non-functional protein.

2. The method of claim 1, wherein the second gene encodes a fluorescent protein or enzyme or auto-fluorescent protein or a protein that provides antibiotic-resistance to the cell.

3. The method of claim 2, wherein the protein encoded by the second gene is a fluorescent protein.

4. The method of claim 3, wherein the fluorescent protein is selected from the group consisting of an mKO fluorescent protein, a green fluorescent protein, a cyan fluorescent protein, a red fluorescent protein, red fluorescent protein variants, and a yellow fluorescent protein.

5. The method of claim 1, wherein the first gene encodes an enzyme and the partition further comprises a substrate for the enzyme.

6. The method of claim 5, wherein the enzyme is selected from the group consisting of beta-galactosidase, luciferase, a target specific protease and a suicide enzyme.

7. The method of claim 6, wherein the enzyme is beta-galactosidase and wherein the partition further comprises an inducer for inducing the expression of the beta-galactosidase.

8. The method of claim 7, wherein the inducer is selected from the group consisting of isopropyl beta-D-1-thiogalactopyranoside, methyl-beta-D-1-thiogalactopyranoside, lactose and lactose derivatives.

9. The method of claim 6, wherein the enzyme is beta-galactosidase and the partition further comprises substrate for beta-galactosidase is selected from the group consisting of fluorescein di-(beta-D-galactopyranoside), naphthofluorescein di-(beta-D-galactopyranoside), (9H-(1,3-dichloro-9,9-dimethylacridin-2-one-7-yl) beta-D-galactopyranoside), 4-methylumbelliferyl beta-D-galactopyranoside, and resorufin beta-D-galactopyranoside.

10. The method of claim 1, wherein the first gene encodes a toxin and the plasmid further includes a gene that encodes an antitoxin.

11. The method of claim 10, wherein the toxin is CcdB and the antitoxin is CcdA.

12. The method of claim 10, wherein the toxin is MazF and the antitoxin is MazE.

13. The method of claim 10, wherein the toxin is HicA and the antitoxin is HicB.

14. The method of claim 1, wherein the cell is selected from the group consisting of a bacterial cell, a mammalian cell, a yeast cell, and an insect cell.

15. The method of claim 1, wherein the polymerase is a DNA polymerase.

16. The method of claim 1, wherein the polymerase is a reverse transcriptase.

17. The method of claim 1, wherein the plasmid is selected from the group consisting of double-stranded DNA plasmid, double-stranded RNA plasmid, a DNA/RNA hybrid plasmid, and a phagemid.

18. A method for determining a polymerase fidelity, the method comprising:
(a) filling a gapped plasmid with a polymerase to form a gap-filled plasmid, wherein the gap-filled plasmid comprises a first gene encoding a protein that is functional or non-functional depending on the polymerase fidelity and a second gene encoding a protein for detecting the presence of a host cell in a partition in step (d),
(b) transforming a host cell with the gap-filled plasmid, wherein the host cell is cultured under conditions for protein expression;
(c) forming a plurality of partitions from a solution comprising the host cell, wherein the plurality of partitions is a plurality of droplets;
(d) detecting the presence of a transformed host cell in one or more of the partitions;
(e) detecting the presence or absence of the functional protein in one or more of the partitions; and
(f) determining the polymerase fidelity by determining a ratio of partitions containing the functional protein to partitions containing a non-functional protein.

19. The method of claim 18, wherein the second gene encodes a fluorescent protein or enzyme or auto-fluorescent protein or a protein that provides antibiotic-resistance to the cell.

20. The method of claim 19, wherein the protein encoded by the second gene is a fluorescent protein.

21. The method of claim 20, wherein the fluorescent protein is selected from the group consisting of an mKO fluorescent protein, a green fluorescent protein, a cyan fluorescent protein, a red fluorescent protein, red fluorescent protein variants, and a yellow fluorescent protein.

22. The method of claim 18, wherein the first gene encodes an enzyme and the partition further comprises a substrate for the enzyme.

23. The method of claim 22, wherein the enzyme is selected from the group consisting of beta-galactosidase, luciferase, a target specific protease and a suicide enzyme.

24. The method of claim 23, wherein the enzyme is beta-galactosidase and wherein the partition further comprises an inducer for inducing the expression of the beta-galactosidase.

25. The method of claim 24, wherein the inducer is selected from the group consisting of isopropyl beta-D-1-thiogalactopyranoside, methyl-beta-D-1-thiogalactopyranoside, lactose and lactose derivatives.

26. The method of claim 23, wherein the enzyme is beta-galactosidase and the partition further comprises substrate for beta-galactosidase is selected from the group consisting of fluorescein di-(beta-D-galactopyranoside), naphthofluorescein di-(beta-D-galactopyranoside), (9H-(1, 3-dichloro-9,9-dimethylacridin-2-one-7-yl) beta-D-galactopyranoside), 4-methylumbelliferyl beta-D-galactopyranoside, and resorufin beta-D-galactopyranoside.

27. The method of claim 18, wherein the first gene encodes a toxin and the plasmid further includes a gene that encodes an antitoxin.

28. The method of claim 27, wherein the toxin is CcdB and the antitoxin is CcdA.

29. The method of claim 27, wherein the toxin is MazF and the antitoxin is MazE.

30. The method of claim 27, wherein the toxin is HicA and the antitoxin is HicB.

31. The method of claim 18, wherein the cell is selected from the group consisting of a bacterial cell, a mammalian cell, a yeast cell, and an insect cell.

32. The method of claim 18, wherein the polymerase is a DNA polymerase.

33. The method of claim 18, wherein the polymerase is a reverse transcriptase.

34. The method of claim 18, wherein the plasmid is selected from the group consisting of double-stranded DNA plasmid, double-stranded RNA plasmid, a DNA/RNA hybrid plasmid, and a phagemid.

35. A method for determining a polymerase fidelity, the method comprising:
(a) filling a gapped plasmid with a polymerase to form a gap-filled plasmid, wherein the gap-filled plasmid comprises a first gene encoding a protein that is functional or non-functional depending on the polymerase fidelity and a second gene encoding a protein for detecting the presence of the plasmid in a partition in step (d),
(b) placing the the gap-filled plasmid into a solution comprising components for in vitro transcription and translation;
(c) forming a plurality of partitions from the solution, wherein the plurality of partitions is a plurality of droplets;
(d) detecting the presence of the plasmid in one or more of the partitions;
(e) detecting the presence or absence of the functional protein in one or more of the partitions; and
(f) determining the polymerase fidelity by determining a ratio of partitions containing the functional protein to partitions containing a non-functional protein.

36. The method of claim 35, wherein the second gene encodes a fluorescent protein or enzyme or auto-fluorescent.

37. The method of claim 36, wherein the protein encoded by the second gene is a fluorescent protein.

38. The method of claim 37, wherein the fluorescent protein is selected from the group consisting of an mKO fluorescent protein, a green fluorescent protein, a cyan fluorescent protein, a red fluorescent protein, red fluorescent protein variants, and a yellow fluorescent protein.

39. The method of claim 35, wherein the first gene encodes an enzyme and the partition further comprises a substrate for the enzyme.

40. The method of claim 39, wherein the enzyme is selected from the group consisting of beta-galactosidase, luciferase, a target specific protease and a suicide enzyme.

41. The method of claim 40, wherein the enzyme is beta-galactosidase and wherein the partition further comprises an inducer for inducing the expression of the beta-galactosidase.

42. The method of claim 41, wherein the inducer is selected from the group consisting of isopropyl beta-D-1-thiogalactopyranoside, methyl-beta-D-1-thiogalactopyranoside, lactose and lactose derivatives.

43. The method of claim 40, wherein the enzyme is beta-galactosidase and the partition further comprises substrate for beta-galactosidase is selected from the group consisting of fluorescein di-(beta-D-galactopyranoside), naphthofluorescein di-(beta-D-galactopyranoside), (9H-(1, 3-dichloro-9,9-dimethylacridin-2-one-7-yl) beta-D-galactopyranoside), 4-methylumbelliferyl beta-D-galactopyranoside, and resorufin beta-D-galactopyranoside.

44. The method of claim 35, wherein the first gene encodes a toxin and the plasmid further includes a gene that encodes an antitoxin.

45. The method of claim 44, wherein the toxin is CcdB and the antitoxin is CcdA.

46. The method of claim 44, wherein the toxin is MazF and the antitoxin is MazE.

47. The method of claim 44, wherein the toxin is HicA and the antitoxin is HicB.

48. The method of claim 35, wherein the polymerase is a DNA polymerase.

49. The method of claim 35, wherein the polymerase is a reverse transcriptase.

50. The method of claim 35, wherein the plasmid is selected from the group consisting of double-stranded DNA plasmid, double-stranded RNA plasmid, a DNA/RNA hybrid plasmid, and a phagemid.

* * * * *